US007947462B2

(12) United States Patent
Niehrs et al.

(10) Patent No.: US 7,947,462 B2

(45) Date of Patent: May 24, 2011

(54) METHODS FOR IDENTIFYING KREMEN POLYPEPTIDE BINDING PARTNERS

(75) Inventors: Christof Niehrs, Heilelberg (DE); Bingyu Mao, Heidelberg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 12/287,729

(22) Filed: Oct. 10, 2008

(65) Prior Publication Data

US 2009/0192109 A1 Jul. 30, 2009

Related U.S. Application Data

(63) Continuation of application No. 10/509,464, filed as application No. PCT/EP03/03277 on Mar. 28, 2003, now abandoned.

(30) Foreign Application Priority Data

Apr. 17, 2002 (EP) .................................... 02008650

(51) Int. Cl.

| | |
|---|---|
| ***G01N 33/53*** | (2006.01) |
| ***G01N 33/566*** | (2006.01) |
| ***C12Q 1/68*** | (2006.01) |

(52) U.S. Cl. ............... 435/7.2; 435/6; 435/7.1; 436/501

(58) Field of Classification Search ........................ None

See application file for complete search history.

(56) References Cited

U.S. PATENT DOCUMENTS

2001/0036643 A1 11/2001 Holloway

FOREIGN PATENT DOCUMENTS

| | | | |
|---|---|---|---|
| EP | 0 911 399 | A2 | 4/1999 |
| WO | WO 00/77239 | A2 | 12/2000 |
| WO | WO 01/34621 | A1 | 5/2001 |
| WO | WO 02/02603 | A2 | 1/2002 |
| WO | WO 02/066509 | A2 | 8/2002 |
| WO | WO 02/092015 | A2 | 11/2002 |

OTHER PUBLICATIONS

Boyden, Lynn M Ph.D. et al., High Bone Density Due to a Mutation in LDL-Receptor-related Protein 5, The New England Journal of Medicine, 2002, 346: 1513-1521.

Brown Sheryl D et al, Isolation and Characterization of LRP6, a Novel Member of the Low Density Lipoprotein Receptor Gene Family, Biochemical and Biophysical Research Communications, 1998, 248: 879-888.

Database EMBL [Online] Jun. 26, 2001, XP002249432 retrieved from EBI Database accession No. AAB95341.

Database EMBL [Online] Nov. 6, 2001, XP002249370 retrieved from EBI Database accession No. AAM93480.

Fischer Leslie et al, Wnt-3A Enhances Bone Morphogenectic Protein-2-medicated Chondrogenesis of Murine C3H10T1/2 Mesenchymal Cells, Journal of Biological Chemistry, 2002, 277: 30870-30878.

Fujino Takahiro et al, Low-density Lipoprotein Receptor-related Protein 5 (LRP5) is Essential for Normal Cholesterol Metabolism and Glucose-Induced Insulin Secretion, Proc. Natl. Acad. Scie. U S A, 2003, 100: 229-234.

Gong Yaoqin et al, LDL Receptor-Related Protein 5 (LRP5) Affects Bone Accrual and Eye Development, Cell, 2001, 107: 513-523.

Kato Masaki et al, Cbfa1-Independent Decrease in Osteoblast Proliferation, Osteopenia, and Persistent Embryonic Eye Vascularization in Mice Deficient in Lrp5, a Wnt coreceptor, The Journal of Cell Biology, 2002, 157: 303-314.

Little Randall D. et al, A Mutation in the LDL Receptor-related Protein 5 Gene Results in the Autosomal Dominant High-Bone-Mass Trait, Am. J. Hum. Genet, 2002, 70: 11-19.

Mao Bingyu et al, LDL-receptor-related protein 6 is a receptor for Dickkopf Proteins, Nature, 2001, 411: 321-325.

Miller Jeffrey R. et al, Signal Transduction Through β-catenin and Specification of Cell Fate During Embryogenesis, Genes & Development, 1996, 10: 2527-2539.

Nakamura Takahiro et al, Molecular Cloning and Characterization of Kremen, a Novel Kringle-containing Transmembrane Protein, Biochimica et Biophysica Acta, 2001, 1518: 63-72.

Nusse Roel et al, Wnt Genes, Cell, 1992, 69: 1073-1087.

Peifer Mark, β-Catenin as Oncogene: The Smoking Gun, Science, 1997, 275: 1752-1753.

Polakis Paul, Wnt Signaling and Cancer, Genes & Development, 2000, 14: 1837-1851.

Saadi-Kheddouci Sihem et al, Early Development of Polycystic Kidney Disease in Transgenic Mice Expressing an Activated Mutant of the β-catenin Gene, Oncogene, 2001, 20: 5972-5981.

Surendran Kameswaran et al, A Role for Wnt-4 in Renal Fibrosis, Am. J. Physiol. Renal Physiol., 2002, 282: 431-441.

Van Es Johan H et al, You Wnt some, you lose some: Oncogenese in the Wnt signaling pathway, Current Opinion in Genetics & Development, 2003, 13: 28-33.

Yang Yingzi et al, Wnt5a and Wnt5b Exhibit Distinct Activities in Coordinating Chondrocyte Proliferation and Differentiation, Development, 2003, 130: 1003-1015.

Aaron M. Zorn, Wnt Signaling: Antagonistic Dickkopfs, Current Biology, 2001, 11: R592-R595.

Bafico, A. et al (2001) Novel Mechanism of WNT Signalling Inhibition Mediated by Dikkopf-1 Interaction with LRP6/Arrow, Nature Cell Biology, 3:683-686.

Mao, B. et al (2002), Kremen Proteins are Dickkopf Receptors that Regulate Wnt/β-Catenin Signalling, Nature, 417:664-667.

(Continued)

*Primary Examiner* — Christine J Saoud

*Assistant Examiner* — Jon M Lockard

(74) *Attorney, Agent, or Firm* — Klauber & Jackson LLC

(57) ABSTRACT

The present invention relates to a composition useful for the diagnosis and therapy of diseases associated with aberrant expression of the gene encoding the receptor Kremen 1 and/or Kremen 2 e.g. tumors or diseases of the kidneys, bones and eyes, lipid and glucose metabolism and obesity. The present invention also relates to a pharmaceutical composition containing a compound which is capable of modifying (a) the expression of the gene encoding Kremen 1 and/or Kremen 2 or (b) the activity of the Kremen 1 and/or Kremen 2 receptor.

10 Claims, 7 Drawing Sheets

Multiple-alignment of mouse and human kremen DNAs (3-1)

Multiple-alignment of mouse and human kremen DNAs (3-2)

```
mkrm1   GGCCTGGCGA  CCCTCCTCAT  CCTCACAGTC  ACAGCAGTTG  1222
hkrm1   GGTCTGGCAA  CTCTCCTCAT  CCTCACAGTC  ACAGCCATTG  1222
mkrm2   ..........  ..........  ..........  .....AGCTG  1181
hkrm2   GGCGCTGGGG  CAGGGCCTGA  GGGCGGA.CC  GGTGGAGCTG  1223

mkrm1   TCGCAAAGAT  TCTTCTGCAT  GTCAGATTTA  AATCTCATCG  1262
hkrm1   TAGCAAAGAT  ACTTCTGCAC  GTCACATTCA  AATCCCATCG  1262
mkrm2   TCTGCTGGCT  CCAGGAAAAG  GGTCTCTGGC  CATGGGACCT  1221
hkrm2   TCTGCTGGCT  CCGGGAAAAG  GGCCCCCGGC  GCTGGGGGCT  1263

mkrm1   AGTCCCTGCA  TCAGGAGACC  TTAGGGACTG  TCGTCAGCCT  1302
hkrm1   TGTTCCTGCT  TCAGGGGACC  TTAGGCATTG  TCATCAACCA  1302
mkrm2   TCCCGGGGCC  CCGGGAGAAG  CTGGGCTGTG  TGGTACCGCC  1261
hkrm2   TCCAGGGGCC  CCAGGAGAAG  CTGGGCTGTG  TGGTACCAAC  1303

mkrm1   GGGGCTTCTG  GAGATATCTG  GACCATTTTC  TATGAACCTT  1342
hkrm1   GGGACTTCGG  GGGAAATCTG  GAGCATTTTT  TACAAGCCTT  1342
mkrm2   GGCCCCGAGG  GGTGGGGCTG  CCCTGTCCCC  CAGGGGACTC  1301
hkrm2   AGCCCCGAGG  GGTGGCCTTG  CCCTGCTCCC  CCGGGGACCC  1343

mkrm1   CCA..CTACA  ATCTCCATCT  TTAAGAAGAA  GCTCAAGGGT  1380
hkrm1   CCA..CTTCA  ATTTCCATCT  TTAAGAAGAA  ACTCAAGGGT  1380
mkrm2   TCAGGCTGAG  GGTCCTGCTG  CGGGCTACCG  TCCCCTGAGT  1341
hkrm2   CCAGGCTGAG  GGTTCTGCCG  CGGGCTACCG  GCCTCTGAGT  1383

mkrm1   CAGAGTCAAC  AAGATGACCG  CAATCCCCTC  GTGAGTGACT  1420
hkrm1   CAGAGTCAAC  AAGATGACCG  CAATCCCCTT  GTGAGTGACT  1420
mkrm2   GCCTCCAGCC  AGAGCTCCTT  GCGCTCGCTC  GTCTCTGCTC  1381
hkrm2   GCCTCCAGCC  AGAGCTCCCT  GCGCTCGCTC  ATCTCCGCTC  1423

mkrm1   GA---  1422
hkrm1   AA---  1422
mkrm2   TCTGA  1386
hkrm2   TCTGA  1428
```

Multiple-alignment of mouse and human kremen DNAs (3-3)

Fig. 1 c

```
mkrm1    1  MAPPAARLALLSAAALTLAARPAPGPRS.GP...ECFTANGADYRGTQSWTALQG
hkrm1    1  MAPPAARLALLSAAALTLAARPAPSPGL.GP...ECFTANGADYRGTQNWTALQG
mkrm2    1  MGTPHLQGFLLLFPLLLR.LHGASAGSLHSPGLSECFQVNGADYRGHQNYTGPRG
hkrm2    1  MGTQALQGFLFLLPLPLLQPRGASAGSLHSPGLSECFQVNGADYRGHQNRTGPRG

mkrm1   52  .GKPCLFWNETFQHPYNTLKYPNGEGGLGEHNYCRNPDGDVSPWCYVAEHEDGVY
hkrm1   52  .GKPCLFWNETFQHPYNTLKYPNGEGGLGEHNYCRNPDGDVSPWCYVAEHEDGVY
mkrm2   55  AGRPCLFWDQTQQHSYSSASDPQGRWGLGAHNFCRNPDGDVQPWCYVAETEEGIY
hkrm2   56  AGRPCLFWDQTQQHSYSSASDPHGRWGLGAHNFCRNPDGDVQPWCYVAETEEGIY

mkrm1  106  WKYCEIPACQMPGNLGCYKDHGNPPPLTGTSKTSNKLTIQTCISFCRSQRFKFAG
hkrm1  106  WKYCEIPACQMPGNLGCYKDHGNPPPLTGTSKTSNKLTIQTCISFCRSQRFKFAG
mkrm2  110  WRYCDIPTCHMPGYLGCFVDSGAPPALSGPSGTSTKLTVQVCLRFCRMKGYQLAG
hkrm2  111  WRYCDIPSCHMPGYLGCFVDSGAPPALSGPSGTSTKLTVQVCLRFCRMKGYQLAG

mkrm1  161  MESGYACFCGNNPDYWKHGEAASTECNSVCFGDHTQPCGGDGRIILFDTLVGACG
hkrm1  161  MESGYACFCGNNPDYWKYGEAASTECNSVCFGDHTQPCGGDGRIILFDTLVGACG
mkrm2  165  VEAGYACFCGSESDLARGRPAPATDCDQTCFGHPGQLCGGDGRLGIYEVSVGSCQ
hkrm2  166  VEAGYACFCGSESDLARGRLAPATDCDQTCFGHPGQLCGGDGRLGVYEVSVGSCQ

mkrm1  216  GNYSAMARVVYSPDFPDTYATGRVCYWTIRVPGASRTHPNFTLFDIRDSADMVEL
hkrm1  216  GNYSAMSSVVYSPDFPDTYATGRVCYWTIRVPGASHIHFSFPLFDIRDSADMVEL
mkrm2  220  GNWSAPQGVIYSPDFPDEYGPDRNCSWVLGQLGAV.LELTFRLFELADSRDRHEL
hkrm2  221  GNWTAPQGVIYSPDFPDEYGPDRNCSWALGPPGAA.LELTFRLFELADPRDRDEL

mkrm1  271  LDGYTHRVLVRLSGRSRPP.LSPNVSLDFVILYFFSDRINQAQGFAVLYQATKEE
hkrm1  271  LDGYTHRVLARFHGRSRPP.LSPNVSLDFVILYFFSDRINQAQGFAVDYQAVKEE
mkrm2  274  RDVSSGNLLRAFDGAHPPPPGPLRLRTAALLLTFRSDARGHAQGFALTYRGLQDT
hkrm2  275  RDAASGSLLRAFDGARPPPSGPLRLGTAALLLTFRSDARGHAQGFALTYRGLQDA

mkrm1  325  PPQERPAVNQTLAEVITEQANLSVSAAHSSKVLYVITPSPSHPPQTAPGSHSWAP
hkrm1  325  LPQERPAVNQTVAEVITEQANLSVSAARSSKVLYVITTSPSHPPQTVPGSNSWAP
mkrm2  329  VE......GRASPEDSTESLAGDPDGAN.......ASCSP......KPG....AA
hkrm2  330  AE......DPEAPEGSAQTPAAPLDGAN.......VSCSP......RPG....AP

mkrm1  380  SVGANSHRVEGWTVYGLATLLILTVTAVVAKILLHVT.......FKSHRVPASG.
hkrm1  380  PMGAGSHRVEGWTVYGLATLLTLTVTAIVAKILLHVT.......FKSHRVPASG.
mkrm2  361  QASIGARVFSTVTAFSVLLLLLLSLLRLLRRRS.............CLLAPGKGS
hkrm2  362  PAAIGARVFSTVTAVSVLLLLLLGLLRPLRRRCGALGQGLRADRWSCLLAPGKGP

mkrm1  427  .DLRDCRQPGASGDIWTIFYEPSTTISIFKKKLKGQSQ..QDDRNPLVSD-----
hkrm1  427  .DLRDCHQPGTSGEIWSIFYKPSTSISIFKKKLKGQSQ..QDDRNPLVSD-----
mkrm2  403  LAMGPSRGPGRS...WAVWYRRPRGVALPCPPGDSQAEGPAAGYRPLSASSQSSL
hkrm2  417  PALGASRGPRRS...WAVWYQQPRGVALPCSPGDPQAEGSAAGYRPLSASSQSSL

mkrm1  474  -------
hkrm1  474  -------
mkrm2  455  RSLVSAL
hkrm2  469  RSLISAL
```

Multiple-alignment of mouse and human Kremen proteins

Fig. 2

METHODS FOR IDENTIFYING KREMEN POLYPEPTIDE BINDING PARTNERS

CROSS REFERENCE TO RELATED APPLICATIONS

The present application is a Continuation of Non-Provisional application Ser. No. 10/509,464, filed Jun. 3, 2005 now abandoned, which, in turn, is a National Stage Application claiming the priority from PCT Application No. PCT/EP03/03277 filed Mar. 28, 2003, which in turn, claims priority from EP Application Serial No. 02 008 650.0, filed Apr. 17, 2002. Applicants claim the benefits of 35 U.S.C. §120 as to the U.S. Non-Provisional application and the PCT application, and priority under 35 U.S.C. §119 as to the said EP application, and the entire disclosures of both applications are incorporated herein by reference in their entireties.

The present invention relates to a composition useful for the diagnosis and therapy of diseases associated with aberrant expression of the gene encoding the receptor Kremen 1 and/or Kremen 2, e.g. tumors, diseases of the kidneys, bones and eyes, lipid and glucose metabolism and obesity. The present invention also relates to a pharmaceutical composition containing a compound which is capable of modifying (a) the expression of the gene encoding Kremen 1 and/or 2 or (b) the activity of the Kremen 1 and/or 2 receptor.

The Wnt signal cascade plays a crucial role as regards regulation of survival, proliferation and differentiation of cells during embryogenesis, and in the adult as shown, e.g., in *Drosophila, Xenopus* and mice (Nusse and Varmus, Cell 69 (1992), 1073-1087). Wnt-genes encode secretory glycoproteins which activate a well characterized signal cascade via a Wnt receptor called "frizzled". In addition to frizzled, Wnts use coreceptors consisting of members of the low density protein receptor related protein (LRP) family, LRP5 and LRP6 to transmit their signals (Zorn, Curr. Biol. 11 (2001), R592-595). LRPs play important roles in various diseases. Most relevant for the present application, in recent studies a new family of proteins, Dkk ("Dickkopf"), could be identified acting as inhibitors of Wnt. DKK1 binds and inhibits the Wnt coreceptor LRP 5/6 (Zorn, Curr. Biol. 11 (2001), R592-595) and thus may provide an important tool to diagnose and/or treat LRPS/6 related diseases (WO02092015). Other prominent members of effectors of this signal cascade are beta-catenin as wells the APC tumor suppressor gene (Miller and Moon, Genes Dev. 10 (1996), 2527-2539).

The Wnt signalling cascade and its components play an important role in various diseases which makes it desirable to modulate its activity:

i) Cancer

Tumorigenesis represents a complex multistage process in which genetic changes and environmental factors are thought to deregulate the cellular processes that control cell proliferation and differentiation. Several studies indicate that an aberrant Wnt signal cascade is involved in the development of colon cancer, breast cancer and melanoma (Pfeifer, Science, 275 (1997), 1752-1753; Polakis, Genes Dev. 14 (2000), 1837-1851). The first gene encoding a protein of the Wnt signal cascade, int-1, was isolated from mouse mammary tumor virus (MMTV) and it could be shown that it is an oncogene. It is thus well established that an aberrant regulation of the activity of Wnt and/or components of the Wnt signal cascade downstream of the Wnt signal, e.g., beta-catenin and APC, are involved in tumorigenesis.

ii) Bone Disease

Wnts signals promote bone formation (e.g. Yang, Development, 130 (2003), 1003-15; Fischer, J. Biol. Chem. 277 (2002) 30870-30878). Consistent with this notion, a gain-of-function mutation of the Wnt receptor LRPS, that leads to resistance to Dkk1 inhibition, causes high bone disease (Boyden, et al., 346 (2002) N Engl J Med, 1513-21; Little, et al., 70 (2002) Am J Hum Genet, 11-9). Conversely, inactivating mutations in LRP5 leads to osteoporosis-pseudoglioma syndrome in humans (Kato, et al., 157 (2002) J Cell Biol, 303-14; Gong, et al., 107 (2001) Cell, 513-23).

iii) Eye Disease

Inactivating mutation in the Wnt receptor LRPS lead to pseudoglioma in humans and eye malformations in mice (Kato, et al., 157 (2002) J Cell Biol 303-314; Gong, et al., 107 (2001) Cell, 513-523).

iv) Kidney

Aberrant Wnt signalling is involved in renal fibrosis (Surendran, Am J Physiol Renal Physiol 282 (2002) 431-441) and polycystic kidney disease (Saadi-Kheddouci, Oncogene 20 (2001) 5972-5981).

v) Lipid and Glucose Metabolism, Obesity

LRPS deficiency in mice leads to increased plasma cholesterol levels in mice fed a high-fat diet, because of the decreased hepatic clearance of chylomicron remnants. In addition, when fed a normal diet, LRP5-deficient mice show a markedly impaired glucose tolerance (Fujino, et al., 100 (2003) Proc Natl Acad Sci USA, 229-234.) Administration of the LRP5 antagonist Dkk1 to mice reduces glucose uptake in various cell line and decreases fat deposition (WO 02/066509).

It is thus clear from the above that Wnt/LRP signalling and antagonism by dkks is involved in a variety of human diseases. Little is known about the mechanism of modulation of the Wnt/LRP signal cascade by inhibitors of the dkk family.

Accordingly, means for the therapy or diagnosis of diseases associated with a dis-regulated signal cascade were not available. Thus, the use of reliable diagnostic molecular markers would be helpful for an understanding of the molecular basis of diseases associated with an aberrant Wnt signal cascade. It can be expected that such markers are also useful for therapy and for the development of novel therapeutic avenues for treatment of Wnt signal cascade dependent diseases, as detailed above.

Thus, the technical problem underlying the present invention is to provide means for diagnosis and therapy of diseases associated with an aberrant Wnt signal cascade.

The solution to said technical problem is achieved by providing the embodiments characterized in the claims. During the experiments resulting in the present invention two genes, kremen 1 and 2, could be identified the products of which bind with high affinity to the polypeptides Dkk1 and Dkk2, which themselves are modulators of the Wnt receptors LRP5 and LRP6. It could be shown that this binding is of physiological relevance since cotransfection of cells with dkk1 as well as kremen 1 and 2 results in a synergistic inhibition of activation of the Wnt signal cascade. These data show that Kremen (1 and 2) can be regarded as a receptor for the Dkk polypeptides and that the biological function of Kremen is the mediation of inhibition of the Wnt-LRP signal cascade via Dkk polypeptides. The data obtained provide evidence that the expression of kremen is very widespread and that the genes encoding Kremen are involved in a variety of biological functions. Thus, Kremen is useful for the diagnosis and the development of therapies for Wnt-LRP mediated diseases, including but not limited to tumor suppression, bone formation, cholesterol and glucose metabolism (including diabetes), obesity, kidney disease and eye disease. It can be expected that, e.g., the inhibition of the Wnt signal cascade by increasing the expression of kremen and/or by stimulating the activity of the polypeptide itself might have a therapeutic effect. Likewise, it can be expected that, e.g., the activation of the Wnt signal cascade by decreasing the expression of kremen and/or by repressing the activity of the polypeptide itself might have a therapeutic effect. On the other hand, the Kremen receptor (or the gene encoding it) can be regarded as a drug target allowing the identification of compounds useful for therapy.

BRIEF DESCRIPTION OF THE DRAWINGS

FIG. 2 illustrates alignment of proteins encoded by mkrm1, hkrm1, mkrm2 and hkrm2. mKremen 1, which is encoded by mkrm1 has amino acid sequence SEQ ID NO: 5; hKremen1 which is encoded by hkrm1 has amino acid sequence SEQ ID NO: 6; mKremen 2, which is encoded by mkrm2, has amino acid sequence SEQ ID NO: 7; and hKremen 2, which is encoded by hkrm2, has amino acid sequence SEQ ID NO: 8. Identical amino acids are highlighted in black, similar amino acids are in grey.

293T cells were transfected with cytomegalovirus (CMV) promoter-driven expression plasmids encoding mkzm1 (top) or mkrm2 (bottom) as indicated, incubated with recombinant Dkk1-AP, Dkk2-AP or Dkk3-AP and stained for bound AP activity. TOP: Binding curves and Scatchard analysis of Dkk-AP fusion proteins binding to mkrm2 transfected cells. Bottom: Binding curves for Dkk-APs binding to mfkrm1 transfected cells. Dissociation constants ($K_d$) are indicated; a, c: Binding curves; b, d, e: Scatchard analysis.

Figure 4:
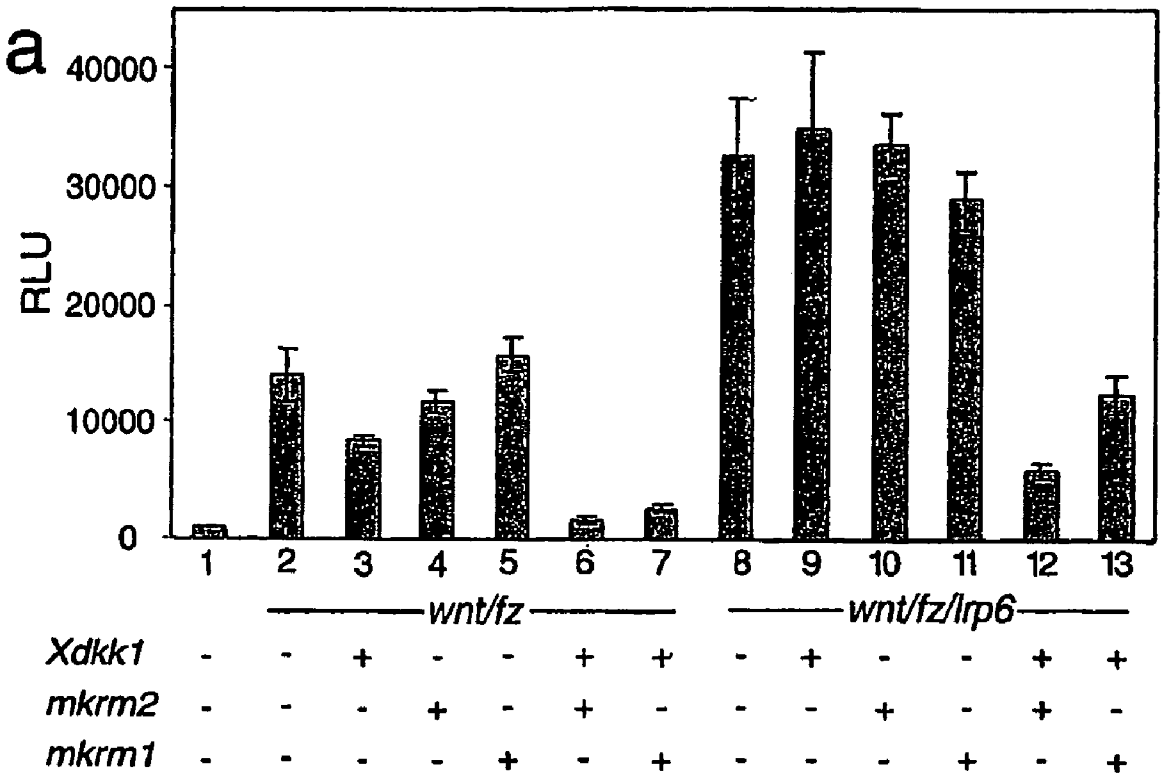

FIG. 4: Kremen and Dkk1 synergistically inhibit the Wnt signal cascade 293 kidney cells were transfected with the Wnt reporter (TOP-FLASH) with or without the genes indicated. Two days after transfection, the luciferase activity expressed was determined. RLU: relative light units (normalized against cotransfected *Renilla luciferase*). Xdkk1=*Xenopus* dkk1; mkrm1, 2=mouse kremen 1,2; wnt=mouse wnt1; fz=mouse frizzled8; lrp6=human lrp6.

Figure 5:
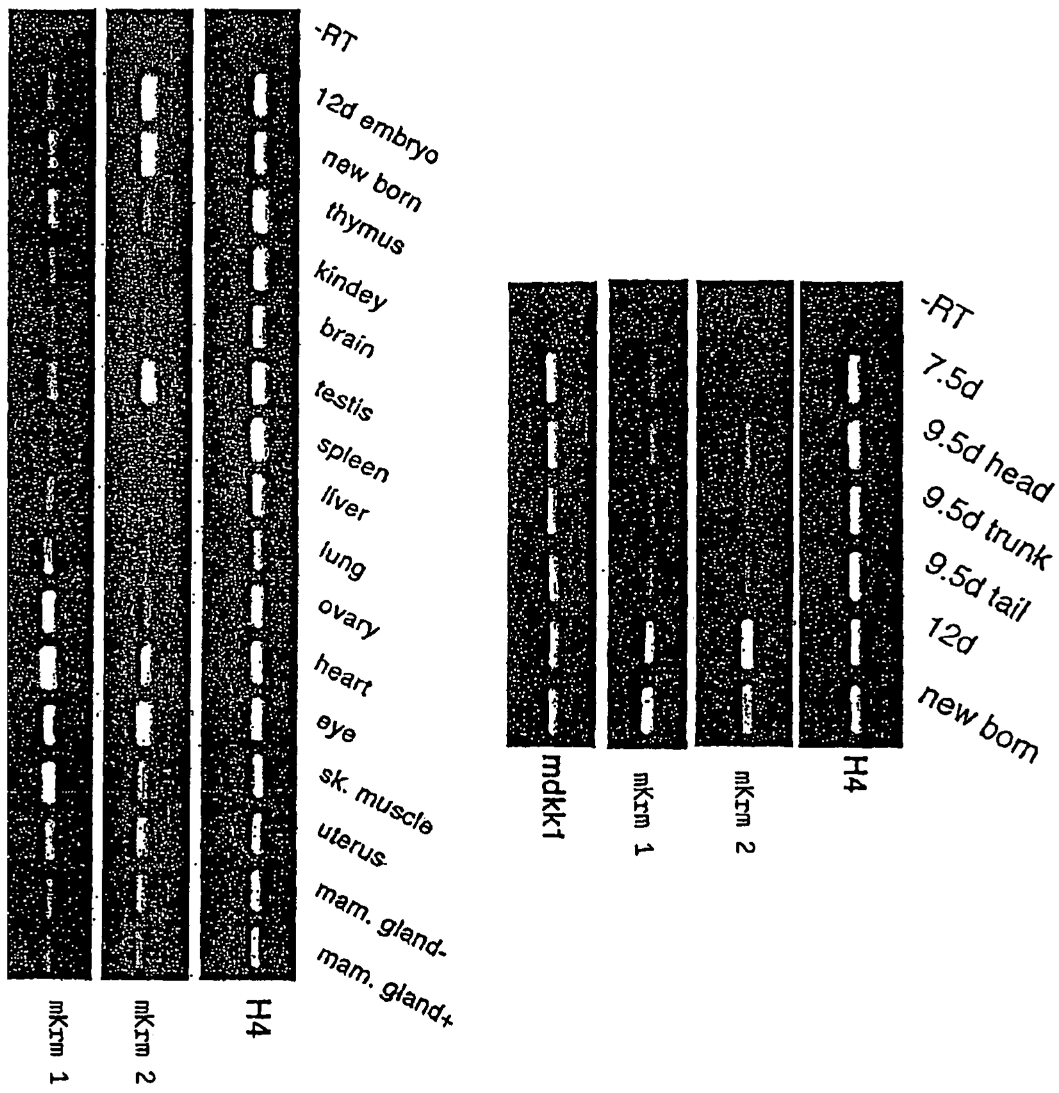

FIG. 5: Expression of kremen in mice

The expression of kremen 1 and kremen 2 was analysed by RT-PCR in various tissues of adult mice. The results were normalized using constitutive histon H4 expression. Abbreviations:—RT=control sample in which reverse transcriptase was omitted; sk muscle=skeletal muscle; mam. glands mammary gland; H4=Histone 4 as loading control; mkrm1, 2=mouse kremen 1,2.

Figure 1:
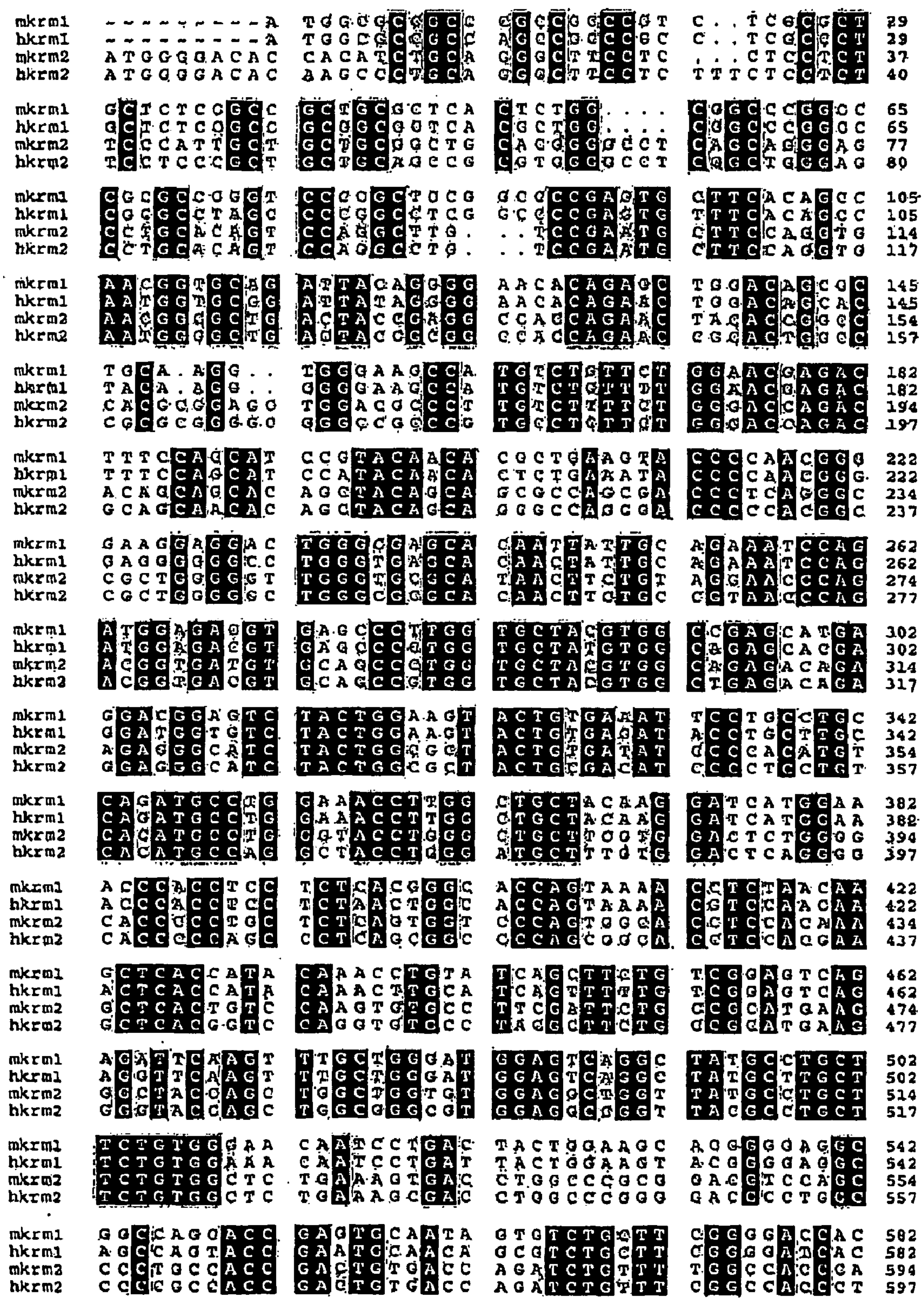
FIGS. 1*a*-1*c* illustrate four contiguous cDNA sequences aligned to show homology. mkrm1 (SEQ ID NO: 1) is cDNA encoding Kremen 1 from mouse; hkrm1 (SEQ ID NO: 2) is cDNA encoding Kremen 1 from human; mkrm2 (SEQ ID NO: 3) is cDNA encoding Kremen2 from mouse; hkrm2 (SEQ ID NO: 4) is cDNA encoding Kremen 2 for human. hkrm1 and hkrm2 are deduced from the human genome sequence in public databases. Identical nucleotides are highlighted in black. All nucleic acid sequences begin with the translation initiator ATG codon.
Figure 1B:
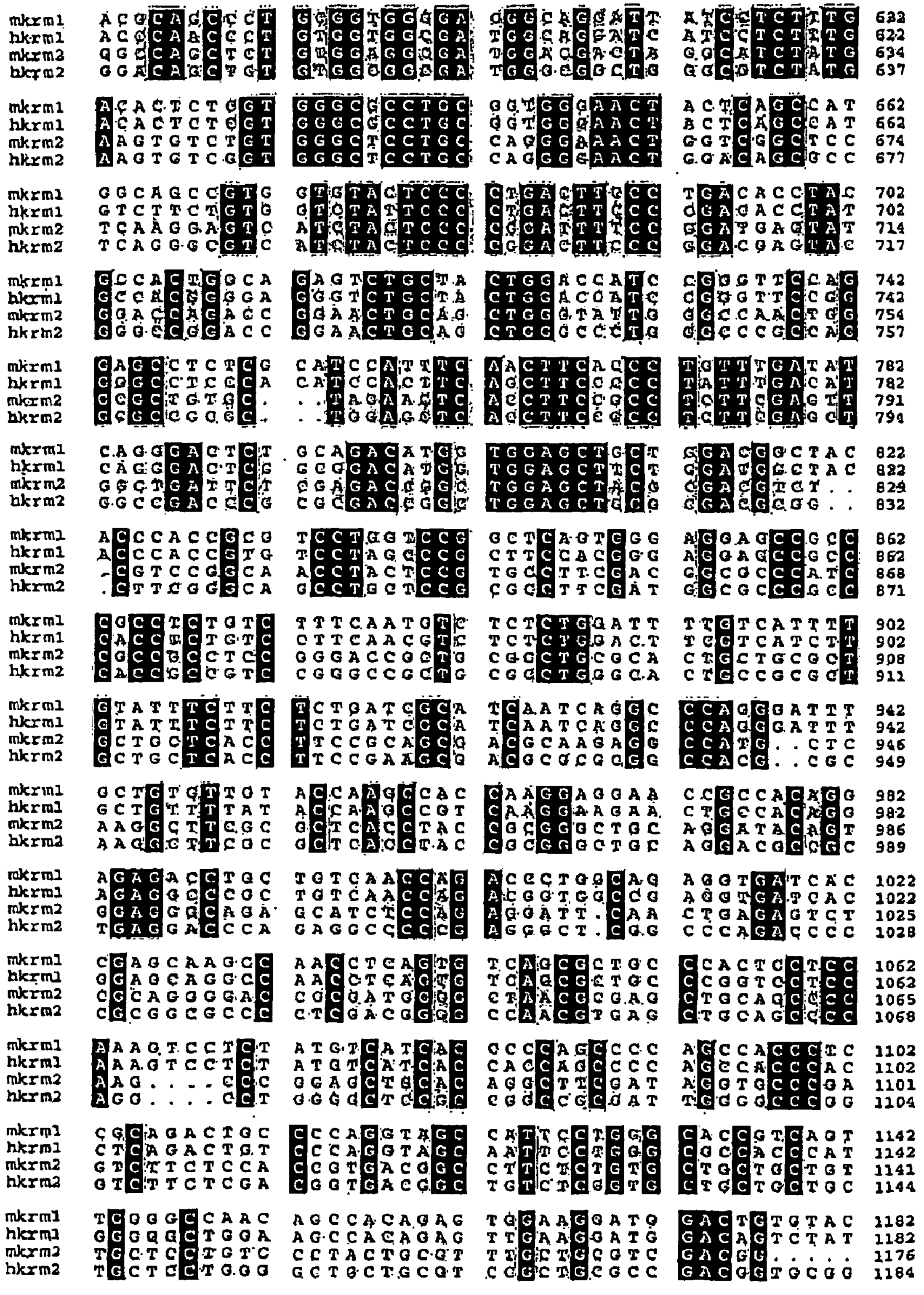

The present invention relates to a diagnostic composition comprising (a) at least one nucleic acid molecule which is capable of specifically hybridizing to the nucleotide sequence encoding Kremen 1 as depicted in FIG. 1 and/or to the nucleotide sequence encoding Kremen 2 as depicted in FIG. 2, or (b) at least one ligand which is capable of specifically binding to a Kremen 1 and/or Kremen 2 polypeptide.

As used herein the term "Kremen 1 polypeptide" and "Kremen 2 polypeptide" not only refers to polypeptides encoded by the nucleotide sequence as depicted in FIGS. 1 and/or 2 but also to polypeptides differing in amino acid sequence due to insertion, deletion and/or substitution of one or more amino acids and showing at least one biological activity of a Kremen 1 and/or Kremen 2 receptor, e.g. the ability of signal transduction after ligand binding. Preferably, the related polypeptides are polypeptides the amino acid sequence of which shows an identity of at least 40%, in particular an identity of at least 65%, preferably of at least 80% and, particularly preferred, of at least 90% to the amino acid sequences of the polypeptides encoded by the nucleotide sequences shown in FIG. 1 or 2.

The nucleic acid molecules useful as probes can be both DNA and RNA molecules, preferably they are single-stranded DNA molecules. They can be isolated from natural sources or can be synthesized according to known methods.

As a hybridization probe nucleic acid molecules can be used, for example, that have a nucleotide sequence which is exactly or basically complementary to a nucleotide sequence as depicted in FIGS. 1 and 2, respectively, or parts of these sequences. The fragments used as hybridization probe can be synthetic fragments that were produced by means of conventional synthetic methods As used herein, the term "hybridizing" relates to hybridization under conventional hybridization conditions, preferably under stringent conditions as described, for example, in Sambrook et al., Molecular Cloning, A Laboratory Manual $2^{nd}$ edition (1989) Cold Spring Harbor Laboratory Press, Cold Spring Harbor, N.Y. However, in certain cases, a hybridizing nucleic acid molecule can also be detected at lower stringency hybridization conditions. Changes in the stringency of hybridization and signal detection are primarily accomplished through the manipulation of formamide concentration (lower percentages of formamide result in lowered stringency), salt conditions, or temperature. For example, lower stringency conditions include an overnight incubation at 37° C. in a solution comprising 6×SSPE (20×SSPE=3M NaCl; 9.2M $NaH_2PO_4$; 0.02M EDTA, pH7.4), 0.5% SDS, 30% formamide, 100 μg/ml salmon sperm blocking DNA, following by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. The inclusion of specific blocking reagents may require modification of the hybridization conditions described above, due to problems with compatibility.

The term "ligand" as used herein refers to any molecule which is capable of specifically binding to Kremen 1 and/or Kremen 2, thus allowing to determine the level of receptor molecules. Examples of such molecules include antibodies, oligonucleotides, proteins or small molecules. The molecule can be the natural ligand of Kremen, i.e. Dkk1 or Dkk2, or can be closely related to said ligand, e.g., a fragment of the ligand, or a natural substrate, a ligand, a structural or functional mimetic; see, e.g., Coligan, Current Protocols in Immunology 1(2) (1991); Chapter 5. In either case, the molecule can be isolated or rationally designed using known techniques; see also infra.

Preferably, the ligand is an antibody. The term "antibody", preferably, relates to antibodies which consist essentially of pooled monoclonal antibodies with different epitopic specificities, as well as distinct monoclonal antibody preparations. Monoclonal antibodies are made from an antigen containing fragments of Kremen 1 or Kremen 2 by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab') 2 fragments) which are capable of specifically binding to Kremen. Fab and f(ab')2 fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a FAB or other immunoglobulin expression library. Moreover, antibodies of the present invention include chimerical, single chain, and humanized antibodies.

For certain purposes, e.g. diagnostic methods, the nucleic acid molecule used as probe or the ligand, e.g., antibody, can be detectably labeled, for example, with a radioisotope, a bioluminescent compound, a chemiluminescent compound, a fluorescent compound, a metal chelate, or an enzyme.

The nucleic acid molecules can be used, for example, as probes or primers in the diagnostic assays described below and allow, e.g., the analysis of the expression of kremen 1 and 2 by determining the mRNA level or the determination of mutations within the coding region or regulatory regions leading to polypeptide molecules with altered, e.g. destroyed, activity, or leading to altered expression. Preferably, the nucleic acid molecules are oligonucleotides having a length of at least 10, in particular of at least 15 and particularly preferred of at least 50 nucleotides. These nucleic acid molecules of the invention can also be used, for example, as primers for a PCR reaction.

The present invention also relates to the use of a nucleic acid molecule or ligand as defined above for the preparation of a diagnostic composition for the diagnosis of a disease associated with (a) aberrant expression of kremen 1 and/or kremen 2 and/or (b) aberrant activity of a Kremen 1 and/or Kremen 2 polypeptide.

In a preferred embodiment, the target to which the nucleic acid molecule hybridizes is an mRNA.

The present invention also provides a method of diagnosing a disease associated with (a) aberrant expression of kremen 1 and/or kremen 2 and/or (b) aberrant activities or amounts of a Kremen 1 and/or Kremen 2 polypeptide in a subject comprising:

(a) determining (a) the amount of expression of kremen 1 and/or kremen 2 and/or (b) the amount of biologically active Kremen 1 and/or Kremen 2 polypeptide in a biological sample; and (b) diagnosing a disease associated with (a) aberrant expression of kremen 2 and/or kremen 2 and/or (b) aberrant activities or amounts of a Kremen 1 and/or Kremen 2 polypeptide or a risk for the development of such disease based on an altered amount of expression of kremen 1 and/or kremen 2 and/or (b) altered activities or amounts of biologically active Kremen 1 and/or Kremen 2 polypeptide compared to a control.

Suitable assay formats are well known to the person skilled in the art and, in addition, described below. Suitable positive control samples expressing human kremen 1 and 2 protein are, e.g., HEK 293 cells.

The Kremen 1 or 2 polypeptide or the corresponding mRNA, e.g. in biological fluids or tissues, may be detected directly in situ, e.g. by in situ hybridization or it may be isolated from other cell components by common methods known to those skilled in the art before contacting with a probe. Detection methods include Northern Blot analysis, RNase protection, in situ methods, e.g. in situ hybridization, in vitro amplification methods (PCR, LCR, QRNA replicase or RNA-transcription/amplification (TAS, 3SR), reverse dot blot disclosed in EP-B1 O 237 362), immunoassays, Western Blot and other detection assays that are known to those skilled in the art.

The probe (e.g. a specific antibody or specific oligonucleotide) of the diagnostic composition can be detectably labeled. In a preferred embodiment, said diagnostic composition contains an anti-Kremen 1 or -Krmen-2 antibody and allows said diagnosis, e.g., by ELISA and contains the antibody bound to a solid support, for example, a polystyrene microtiter dish or nitrocellulose paper, using techniques known in the art. Alternatively, said diagnostic compositions are based on a RIA and contain said antibody marked with a radioactive isotope. Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium rhodamine, and biotin. In addition to assaying Kremen levels in a biological sample, the polypeptide can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. A protein-specific antibody or antibody fragment which has been labeled with an appropriate detectable imaging moiety, such as a radioisotope (for example, $^{131}I$, $^{112}In$, $^{99}mTc$), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}mTc$. The labeled antibody or antibody fragment will then preferentially accumulate at the location of cells which contain the specific Kremen polypeptide. In vivo tumor imaging is, e.g., described in S. W. Burchiel et al., "Immunopharmacokinetics of Radiolabeled Antibodies and Their Fragments". (Chapter 13 in Tumor Imaging: The Radiochemical Detection of Cancer, S. W. Burchiel and B. A. Rhodes, eds., Masson Publishing Inc. (1982)).

In a further aspect, the present invention, relates to a method for identifying a binding partner to a Kremen 1 and/or 2 polypeptide comprising:

(a) contacting said polypeptide with a compound to be screened; and (b) determining whether the compound effects an activity of the polypeptide.

The invention also includes a method of identifying compounds which bind to a Kremen 1 and/or Kremen 2 polypeptide comprising the steps of:

(a) incubating a candidate binding compound with said polypeptide; and (b) determining if binding has occurred.

Kremen 1 or 2 polypeptides may be used to screen for proteins or other compounds that bind to Kremen 1 or 2 or for proteins or other compounds to which Kremen 1 and 2 bind. The binding of Kremen 1 or 2 and the molecule may activate (agonist), increase, inhibit (antagonist), or decrease activity of Kremen 1 or Kremen 2 or the molecule bound. Examples of such molecules include antibodies, oligonucleotides, proteins (e.g., ligands), or small molecules.

Preferably, the molecule is closely related to the natural ligand of Kremen 1 or 2, e.g., a fragment of the ligand, or a natural substrate, a ligand, a structural or functional mimetic; see, e.g., Coligan, Current Protocols in Immunology 1(2) (1991); Chapter 5.

Preferably, the screening for these molecules involves producing appropriate cells which express Kremen 1 and/or, either as a secreted protein or on the cell membrane. Preferred cells include cells from mammals, yeast, *Drosophila*, or *E. coli*. Cells expressing Kremen 1 and/or 2 (or cell membrane containing the expressed polypeptide) are then preferably contacted with a test compound potentially containing the molecule to observe binding, stimulation, or inhibition of activity of Kremen 1 and/or 2.

The assay may simply test binding of a candidate compound to Kremen 1 and/or 2, wherein binding is detected by a label, or in an assay involving competition with a labeled competitor. Further, the assay may test whether the candidate compound results in a signal generated by binding to Kremen 1 and/or Kremen 2. Suitable assays to analyze the activity of kremen 1 and/or 2 include Wnt-inducible luciferase reporter assays in transfected HEK 293 cells, where dkk1 synergizes with kremen 1 and/or 2 to inhibit a Wnt1-induced signal, such as is shown in FIG. 4.

Alternatively, the assay can be carried out using cell-free preparations, polypeptide/molecule affixed to a solid support, chemical libraries, or natural product mixtures. The assay may also simply comprise the steps of mixing a candidate compound with a solution containing Kremen 1 and/or Kremen 2, measuring Kremen/molecule activity or binding, and comparing the Kremen/molecule activity or binding to a standard.

Preferably, an ELISA assay can measure Kremen 1 and/or Kremen 2 level or activity in a sample (e.g., biological sample) using a monoclonal or polyclonal antibody. The antibody can measure Kremen 1 and/or Kremen 2 level or activity by either binding; directly or indirectly, to Kremen 1 and/or Kremen 2 or by competing with Kremen 1 and/or Kremen 2 for a substrate. All of these above assays can be used as diagnostic or prognostic markers. The molecules discovered using these assays can be used to treat disease or to bring about a particular result in a patient (e.g., elimination of a tumor, support of regenerative processes etc.) by modulating, preferably activating the Kremen 1 and/or Kremen 2 molecule. Moreover, the assays can discover agents which may inhibit or enhance the production of Kremen 1 and/or Kremen 2 from suitably manipulated cells or tissues.

Moreover, the invention includes a method of identifying activators/agonists or inhibitors/antagonists of a Kremen 1 and/or Kremen 2 polypeptide comprising the steps of:

(a) incubating a candidate compound with said polypeptide;
(b) assaying a biological activity, and
(c) determining if a biological activity of said polypeptide has been altered.

Suitable assays include analysis of formation of a ternary complex between kremen1 or kremen 2 with recombinant Dkk1 protein and recombinant extracellular domain of LRP6.

In a further embodiment, the present invention relates to method of identifying and obtaining a drug candidate for therapy of diseases associated with (a) aberrant expression of kremen 1 and/or kremen 2 and/or (b) aberrant activities or amounts of a Kremen 1 and/or Kremen 2 polypeptide comprising the steps of (a) contacting a Kremen 1 and/or Kremen 2 polypeptide or a cell expressing said polypeptide, and optionally the corresponding ligand(s), in the presence of components capable of providing a detectable signal in response to binding to said drug candidate to be screened; and
(b) detecting presence or absence of a signal or increase of the signal generated, wherein the presence or increase of the signal is indicative for a putative drug.

Suitable assays to analyze the activity of kremen 1 and/or 2 include Wnt-inducible luciferase reporter assays in transfected HEK 293 cells, where dkk1 synergizes with kremen 1 and/or 2 to inhibit a Wnt1-induced signal, such as is shown in FIG. 4.

The drug candidate may be a single compound or a plurality of compounds. The term "plurality of compounds" in a method of the invention is to be understood as a plurality of substances which may or may not be identical.

Said compound or plurality of compounds may be chemically synthesized or microbiologically produced and/or comprised in, for example, samples, e.g., cell extracts from, e.g., plants, animals or microorganisms. Furthermore, said compound(s) may be known in the art but hitherto not known to be capable of suppressing or activating Kremen 1 and/or Kremen 2 polypeptides. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994) and in the appended examples. The plurality of compounds may be, e.g., added to the reaction mixture, culture medium, injected into a cell or otherwise applied to a transgenic animal. The cell or tissue that may be employed in the method of the invention preferably is a host cell, mammalian cell or non-human transgenic animal.

If a sample containing a compound or a plurality of compounds is identified in the method of the invention, then it is either possible to isolate the compound from the original sample identified as containing the compound capable of suppressing or activating a Kremen 1 and/or Kremen 2 polypeptide, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical.

Several methods are known to the person skilled in the art for producing and screening large libraries to identify compounds having specific affinity for a target. These methods include the phage-display method in which randomized peptides are displayed from phage and screened by affinity chromatography to an immobilized receptor; see, e.g., WO 91/17271, WO 92/01047, U.S. Pat. No. 5,223,409. In another approach, combinatorial libraries of polymers immobilized on a chip are synthesized using photolithography; see, e.g., U.S. Pat. No. 5,143,854, WO 90/15070 and WO 92/10092. The immobilized polymers are contacted with a labeled receptor and scanned for label to identify polymers binding to the receptor. The synthesis and screening of peptide libraries on continuous cellulose membrane supports that can be used for identifying binding ligands of the Kremen 1 and/or 2 polypeptides and, thus, possible inhibitors and activators is described, for example, in Kramer, Methods Mol. Biol. 87

(1998), 25-39. This method can also be used, for example, for determining the binding sites and the recognition motifs in the Kremen 1 and/or 2 polypeptide. In like manner, the substrate specificity of the DnaK chaperon was determined and the contact sites between human interleukin-6 and its receptor; see Rudiger, EMBO J. 16 (1997), 1501-1507 and Weiergraber, FEBS Lett. 379 (1996), 122-126, respectively. Furthermore, the above-mentioned methods can be used for the construction of binding supertopes derived from the Kremen 1 or Kremen 2 polypeptide. A similar approach was successfully described for peptide antigens of the anti-p24 (HIV-1) monoclonal antibody; see Kramer, Cell 91 (1997), 799-809. A general route to fingerprint analyses of peptide-antibody interactions using the clustered amino acid peptide library was described in Kramer, Mol. Immunol. 32 (1995), 459-465. In addition, antagonists of a Kremen 1 and/or Kremen 2 polypeptide can be derived and identified from monoclonal antibodies that specifically react with a Kremen 1 and/or Kremen 2 polypeptide in accordance with the methods as described in Doring, Mol. Immunol. 31 (1994), 1059-1067.

All these methods can be used in accordance with the present invention to identify activators/agonists and inhibitors/antagonists of a Kremen 1 and/or Kremen 2 polypeptide.

Various sources for the basic structure of such an activator or inhibitor can be employed and comprise, for example, mimetic analogs of a Kremen 1 and/or Kremen 2 polypeptide. Mimetic analogs of a Kremen 1 and/or Kremen 2 polypeptide or biologically active fragments thereof can be generated by, for example, substituting the amino acids that are expected to be essential for the biological activity with, e.g., stereoisomers, i.e. D-amino acids; see e.g., Tsukida, J. Med. Chem. 40 (1997), 3534-3541. Furthermore, in case fragments are used for the design of biologically active analogs pro-mimetic components can be incorporated into a peptide to reestablish at least some of the conformational properties that may have been lost upon removal of part of the original polypeptide; see, e.g., Nachman, Regul. Pept. 57 (1995), 359-370. Furthermore, a Kremen 1 and/or Kremen 2 polypeptide can be used to identify synthetic chemical peptide mimetics that bind to or can function as a ligand, substrate or binding partner of said polypeptide(s) as effectively as does the natural polypeptide; see, e.g., Engleman, J. Clin. Invest. 99 (1997), 2284-2292. For example, folding simulations and computer redesign of structural motifs of a Kremen 1 and/or Kremen 2 polypeptide can be performed using appropriate computer programs (Olszewski, Proteins 25 (1996), 286-299; Hoffman, Comput. Appl. Biosci. 11 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of a Kremen 1 and/or Kremen 2 polypeptide and its ligand or other interacting proteins by computer assistant searches for complementary peptide sequences (Fassina, Immunomethods 5 (1994), 114-120. Further appropriate computer systems for the design of protein and peptides are described in the prior art, for example in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. The results obtained from the above-described computer analysis can be used for, e.g., the preparation of peptide mimetics of a Kremen 1 and/or Kremen 2 polypeptide or fragments thereof. Such pseudopeptide analogues of the natural amino acid sequence of the protein may very efficiently mimic the parent protein (Benkirane, J. Biol. Chem. 271 (1996), 33218-33224). For example, incorporation of easily available achiral ω-amino acid residues into a Kremen 1 or 2 polypeptide or a fragment thereof results in the substitution of amide bonds by polymethylene units of an aliphatic chain, thereby providing a convenient strategy for constructing a peptide mimetic (Banerjee, Biopolymers 39 (1996), 769-777). Superactive peptidomimetic analogues of small peptide hormones in other systems are described in the prior art (Zhang, Biochem. Biophys. Res. Commun. 224 (1996), 327-331). Appropriate peptide mimetics of a Kremen 1 and/or Kremen 2 polypeptide can also be identified by the synthesis of peptide mimetic combinatorial libraries through successive amide alkylation and testing the resulting compounds, e.g., for their binding and immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, a three-dimensional and/or crystallographic structure of a Kremen 1 and/or Kremen 2 polypeptide can be used for the design of peptide mimetic inhibitors of the biological activity of the polypeptide (Rose, Biochemistry 35 (1996), 12933-12944; Rutenber, Bioorg. Med. Chem. 4 (1996), 1545-1558).

It is also well known to the person skilled in the art, that it is possible to design, synthesize and evaluate mimetics of small organic compounds that, for example, can act as a substrate or ligand to a Kremen 1 and/or Kremen 2 polypeptide. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987.

The nucleic acid molecule encoding a Kremen 1 and/or Kremen 2 polypeptide can also serve as a target for activators and inhibitors. Activators may comprise, for example, proteins that bind to the mRNA a gene encoding a Kremen 1 and/or Kremen 2 polypeptide, thereby stabilizing the native conformation of the mRNA and facilitating transcription and/or translation, e.g., in like manner as Tat protein acts on HIV-RNA. Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical interest, and for identifying unknown RNA targets for use in treating a disease. These methods and compositions can be used in screening for novel or for identifying compounds useful to alter expression levels of polypeptides encoded by a nucleic acid molecule. Alternatively, for example, the conformational structure of the RNA fragment which mimics the binding site can be employed in rational drug design to modify known drugs to make them bind more avidly to the target. One such methodology is nuclear magnetic resonance (NMR), which is useful to identify drug and RNA conformational structures. Still other methods are, for example, the drug design methods as described in WO 95/35367, U.S. Pat. No. 5,322,933, where the crystal structure of the RNA fragment can be deduced and computer programs are utilized to design novel binding compounds.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Furthermore, genes encoding a putative regulator of a Kremen 1 and/or Kremen 2 polypeptide and/or which exert their effects up- or downstream a Kremen 1 and/or Kremen 2 polypeptide may be identified using, for example, insertion mutagenesis using, for example, gene targeting vectors known in the art. Said compounds can also be functional derivatives or analogues of known inhibitors or activators. Such useful compounds can be for example transacting factors which bind to a Kremen 1 and/or Kremen 2 polypeptide or regulatory sequences of the gene encoding it. Identification of transacting factors can be carried out using standard methods in the art (see, e.g., Sambrook, supra). To determine whether a protein binds to the protein itself or regulatory sequences, standard native gel-shift analyses can be carried out. In order to identify a transacting factor which binds to the protein or regulatory sequence, the protein or regulatory sequence can be used as an affinity reagent in standard protein purification methods, or as a probe for screening an expression library. The identification of nucleic acid molecules which encode polypeptides which interact with a Kremen 1 and/or Kremen 2 polypeptide described above can also be achieved, for example, as described in Scofield (Science 274 (1996), 2063-2065) by use of the so-called yeast "two-hybrid system". In this system the Kremen 1 or Kremen 2 polypeptide or a smaller part thereof is linked to the DNA-binding domain of the GALA transcription factor. A yeast strain expressing this fusion polypeptide and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of a Kremen 1 and/or Kremen 2 polypeptide, the complex is able to direct expression of the reporter gene. In this way the nucleic acid molecules encoding Kremen 1 and Kremen 2, respectively, and the encoded peptide can be used to identify peptides and proteins interacting with a Kremen 1 and/or Kremen 2 polypeptide.

Once the transacting factor is identified, modulation of its binding to or regulation of expression of a Kremen 1 and/or Kremen 2 polypeptide can be pursued, beginning with, for example, screening for inhibitors against the binding of the transacting factor to a Kremen 1 or Kremen 2 polypeptide. Activation or repression of a Kremen 1 and/or Kremen 2 polypeptide could then be achieved in animals by applying the transacting factor (or its inhibitor) or the gene encoding it, e.g. in an expression vector. In addition, if the active form of the transacting factor is a dimer, dominant-negative mutants of the transacting factor could be made in order to inhibit its activity. Furthermore, upon identification of the transacting factor, further components in the signal cascade leading to activation (e.g. signal transduction) or repression of a gene involved in the control of a Kremen 1 and/or Kremen 2 polypeptide then can be identified. Modulation of the activities of these components can then be pursued, in order to develop additional drugs and methods for modulating the metabolism of protein degradation in animals. Thus, the present invention also relates to the use of the two-hybrid system as defined above for the identification of activators or inhibitors of a Kremen 1 and/or Kremen 2 polypeptide.

The compounds isolated by the above methods also serve as lead compounds for the development of analog compounds. The analogs should have a stabilized electronic configuration and molecular conformation that allows key functional groups to be presented to a Kremen 1 and/or Kremen 2 polypeptide or its ligand in substantially the same way as the lead compound. In particular, the analog compounds have spatial electronic properties which are comparable to the binding region, but can be smaller molecules than the lead compound, frequently having a molecular weight below about 2 kD and preferably below about 1 kD. Identification of analog compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art; see also supra. Furthermore, peptidomimetics and/or computer aided design of appropriate derivatives and analogues can be used, for example, according to the methods described above.

Once the described compound has been identified and obtained, it is preferably provided in a therapeutically acceptable form.

Accordingly, the present invention also relates to a pharmaceutical composition comprising a nucleic acid molecule encoding a Kremen 1 and/or Kremen 2 polypeptide, a Kremen 1 and/or Kremen 2 polypeptide itself, recombinant vector (for examples, see below), antibody, activator/agonist, inhibitor/antagonist and/or binding partner of a Kremen 1 and/or Kremen 2 polypeptide and a pharmaceutically acceptable excipient, diluent or carrier.

Preferably, for therapeutic purposes, the Kremen 1 and/or Kremen 2 polypeptide is recombinantly produced by use of the nucleic acid sequences shown in FIGS. 1 and 2. Suitable vectors for recombinant expression are known to the person skilled in the art. Preferably, they are plasmids, cosmids, viruses, bacteriophages and other vectors usually used in the field of genetic engineering. Vectors suitable for use in the present invention include, but are not limited to the T7-based expression vector for expression in mammalian cells and baculovirus-derived vectors for expression in insect cells. Preferably, the nucleic acid molecule of the invention is operatively linked to the regulatory elements in the recombinant vector of the invention that guarantee the transcription and synthesis of an mRNA in prokryotic and/or eukaryotic cells that can be translated. The nucleotide sequence to be transcribed can be operably linked to a promoter like a T7, metallothionein I or polyhedrin promoter. The host cells used for recombinant expression are prokaryotic or eukaryotic cells, for example mammalian cells, bacterial cells, insect cells or yeast cells. The polypeptide is isolated from the cultivated cells and/or the culture medium. Isolation and purification of the recombinantly produced polypeptide may be carried out by conventional means including preparative chromatography and affinity and immunological separations using, e.g., an anti-Kremen 1 or 2 antibody, or, e.g., can be substantially purified by the one-step method described in Smith and Johnson, Gene 67; 31-40 (1988).

Examples of suitable pharmaceutical carriers etc. are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g.

by intravenous, intraperitoneal, subcutaneous, intramuscular, topical or intradermal administration. The route of administration, of course, depends on the nature of the disease and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of the disease, e.g., tumor, general health and other drugs being administered concurrently.

The delivery of the nucleic acid molecules encoding a Kremen 1 and/or Kremen 2 polypeptide can be achieved by direct application or, preferably, by using a recombinant expression vector such as a chimeric virus containing these compounds or a colloidal dispersion system. Direct application to the target site can be performed, e.g., by ballistic delivery, as a colloidal dispersion system or by catheter to a site in artery. The colloidal dispersion systems which can be used for delivery of the above nucleic acid molecules include macromolecule complexes, nanocapsules, microspheres, beads and lipid-based systems including oil-in-water emulsions (mixed), micelles, liposomes and lipoplexes, The preferred colloidal system is a liposome. Organ-specific or cell-specific liposomes can be used in order to achieve delivery only to the desired tissue. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, e.g., an antibody, a receptor, sugar, glycolipid, protein etc., by well known methods). In the present invention monoclonal antibodies are preferably used to target liposomes to specific tissues, e.g. tumor tissue, via specific cell-surface ligands.

Preferred recombinant vectors useful for gene therapy are viral vectors, e.g. adenovirus, herpes virus, vaccinia, or, more preferably, an RNA virus such as a Retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors.

Further suitable vectors and methods for in vitro- or in vivo-gene therapy are described in the literature and are known to the persons skilled in the art; see, e.g., WO 94/29469 or WO 97/00957.

In order to achieve expression only in the target organ, e.g., a tumor to be treated, the nucleic acid molecules encoding a Kremen 1 and/or Kremen 2 polypeptide can be linked to a tissue specific promoter and used for gene therapy. Such promoters are well known to those skilled in the art (see e.g. Zimmermann et al., (1994) Neuron 12, 11-24; Vidal et al.; (1990) EMBO J. 9, 833-840; Mayford et al., (1995), Cell 81, 891-904; Pinkert et al., (1987) Genes & Dev. 1, 268-76).

The present invention also relates to the use of the above compounds of the invention for the preparation of a pharmaceutical composition for treatment of a disease associated with (a) aberrant expression of kremen 1, kremen 2 and/or genes involved into the Wnt signal cascade, and/or (b) aberrant activities or amounts of a Kremen 1, Kremen 2 and/or a polypeptide involved into the Wnt signal cascade. In a preferred embodiment, said disease is a tumor, preferably breast cancer, a colon carcinoma or a melanoma.

Finally, the present invention relates to the use of a nucleotide molecule encoding a polypeptide having a biological activity of Kremen 1 and/or Kremen 2, a Kremen 1 and/or Kremen 2 polypeptide, an activator/agonist of a Kremen 1 and/or Kremen 2 polypeptide or binding partner of said polypeptide(s) for the preparation of a pharmaceutical composition for inhibiting the Wnt signal cascade which might be useful for supporting regenerative processes in a patient, e.g. growth of tissue like muscle, hair, etc.

The following examples illustrate the invention.

EXAMPLE 1

Isolation of cDNAs Encoding Kremen 1 and 2, Respectively

A mouse 13.5 day embryo cDNA library in the expression vector pCMV-SPORT2 (Gibco BRL) was used to prepare pools of about 250 colonies, and plasmid DNA from each pool was transiently transfected into 293T cells in 24-well plates using FuGENE 6 (Roche). After 48 hours cells were incubated with medium containing 1 nM Dkk1-alkaline phosphatase (Dkk1-AP) fusion protein (Mao et al., Nature 411 (2001) 321-325) and processed for AP histochemistry. From 1500 pools, 2 positive pools were identified and single clones were isolated by sib selection. Sequencing analysis showed that they represent independent isolates of mkremen 2. A full length mouse kremen 1 clone was isolated from the same library by PCR using published nucleotide sequence data (Nakamura et al, Biochim. Biophys. Acta 1518 (2001), 63-72). The open reading frame of mkremen 1 and -2 was cloned into pCS2+ to generate pCS2-mkrm1 and -2. pCS-flag-mkrm2 was constructed by inserting a flag epitope after the signal peptide and was used as template to generate the pCS-flag-mkrm2ΔWSC by PCR.

EXAMPLE 2

The Binding of Kremen 1 and 2 to Dkk1 and Dkk2 Shows High Affinity and is Physiologically Relevant For binding assays 293T cells were transfected (T) with mkrm1 or mkrm2 as indicated, incubated with recombinant Dkk1-alkaline phosphatase fusion protein (Dkk1-AP) or alkaline phosphatase (AP) and stained for bound AP activity. The results are shown in FIG. 3.

As shown in FIG. 4, luciferase Wnt reporter assays in 293T cells were done in 96 well plates at least in triplicates as described (Wu et al., Curr Biol 10 (2000), 1611-1614). Luciferase activity was normalized against *Renilla* activity using a commercial kit (Clonetech). Xdkk1=*Xenopus* dkk1 (Glinka, et al. Nature 391, (1998) 357-362); mkrm1,2=mouse kremen 1,2; wnt=mouse wnt1; fz=mouse frizzled8; lrp6=human lrp6 (Tamai, et al. Nature 407 (2000) 530-535); Wnt luciferase reporter TOP-FLASH (Korinek et al. Science 275 (1997)1784-1787).

Figure 3:
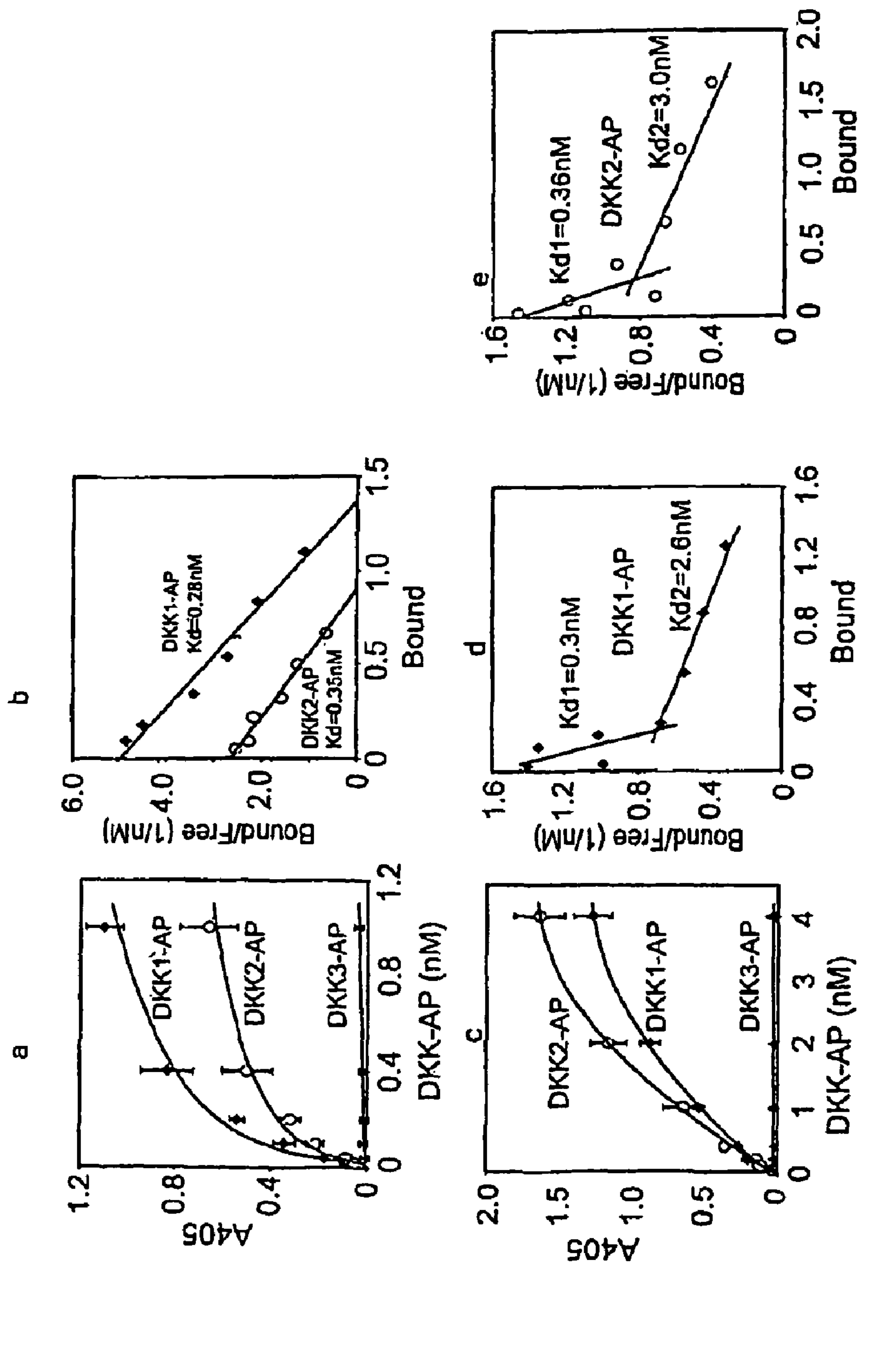
FIG. 3: Kremen is a high affinity receptor for Dkk1 and Dkk2

As shown in FIG. 3, the binding of Dkk alkaline phosphatase fusion protein to Kremen 2 and Kremen 1, respectively, shows high affinity. Moreover, it could be shown that only Dkk1 and Dkk2 bind to Kremen but not Dkk3.

In an additional experiment, 293 kidney cells were transfected with the Wnt reporter (TOP-FLASH) with or without the genes indicated. Two days after transfection, the luciferase activity expressed was determined. As shown in FIG. 4, cotransfection of Wnt and its receptor, frizzled (fz) results in stimulation of the Wnt signal cascade (see FIG. 4, lane 1 versus lane 2) and cotransfection of dkk1 and kremen 1 and kremen 2 leads to synergistic inhibition of this activation of the Wnt signal cascade. This effect is even more pronounced if wnt has been cotransfected with its receptor frizzled (fz) and the co-receptor lrp6. A very strong activation of the Wnt signal cascade (lane 8) can be observed. This activation can only inhibited by cotransfection with dkk1 and kremen 1,2 (lanes 12 and 13) but not by transfection with the single genes (dkk1, lane 9; kremen 2, lane 10; kremen 1, lane 11).

EXAMPLE 3

Determination of the Expression Profile of Kremen 1 and 2 in Various Tissues of Mice The expression of kremen 1 and 2 in various tissues of mice was studied by RT-PCR. RNA isolation from adult mouse organs and RT-PCR assays were carried out in the linear phase of amplification and with histone 4 primers as described (Glinka et al., Nature 389 (1997), 517-519) Other primers were: mkrm1 (f, GTGCTTCACAGCCAACGGTGCA (SEQ ID NO: 9); r, ACGTAGCACCAAGGGCTCACGT (SEQ ID NO: 10)); mkrm2 (f, AGGGAAACTGGTCGGCTC (SEQ ID NO: 11); r, AAGGCACGGAGTAGGTTGC (SEQ ID NO: 12)). Cycle no. were H4: 26 cycles; mkrm1: 35 cycles; mkrm2: 32 cycles. The results show that both kremens are expressed in all mouse tissues tested, but with varying expression level (FIG. 5). Similar results were obtained using *Xenopus* embryos.

What is claimed is:

1. A method for identifying a compound which is a binding partner to a Kremen polypeptide(s) comprising:

a) contacting one or more Kremen 1 polypeptides comprising the amino acid sequence of SEQ ID NO: 5 or SEQ ID NO: 6 or a cell expressing said polypeptide(s) with a compound to be screened; and b) determining if binding has occurred.

2. The method of claim 1 wherein binding is determined by detecting binding by a label of the compound to be screened or in an assay involving competition with a labeled competitor.

3. The method of claim 1 wherein in step a) said polypeptide(s) is further contacted with corresponding ligand Dkk and wherein in step b) binding is determined by detecting the formation of a ternary complex between said polypeptide(s) with Dkk protein, wherein the formation of said ternary complex is altered in the presence of said compound.

4. The method of claim 3 wherein the formation of a ternary complex is determined by contacting with a ligand DKK-AP fusion protein and detecting bound AP activity.

5. The method of claim 3 wherein the formation of said complex is detected in a Wnt-inducible reporter assay, wherein Dkk synergizes with Kremen 1 polypeptide comprising the amino acid sequence of SEQ ID NO: 5 or SEQ ID NO: 6 to inhibit a Wnt-induced signal.

6. A method according to claim 1, wherein the compound to be screened is an antibody that binds Kremen 1 polypeptide.

7. A method according to claim 1, wherein the compound to be screened is a small molecule.

8. A method according to claim 1, wherein the compound to be screened is a nucleic acid.

9. A method according claim 1, wherein the method utilizes cells which express Kremen 1.

10. A method according to claim 1, wherein the method is carried out using a cell-free preparation.

* * * * *

SEQUENCE LISTING

<160> NUMBER OF SEQ ID NOS: 12

<210> SEQ ID NO 1
<211> LENGTH: 1422
<212> TYPE: DNA
<213> ORGANISM: Mus musculus

<400> SEQUENCE: 1
atggcgccgc ccgccgcccg tctcgcgctg ctctccgccg ctgcgctcac tctggcggcc 60
cggcccgcgc ccggtccccg ctccggcccc gagtgcttca cagccaacgg tgcagattac 120
aggggaacac agagctggac agcgctgcaa ggtgggaagc catgtctgtt ctggaacgag 180
actttccagc atccgtacaa cacgctgaag taccccaacg gggaaggagg actgggcgag 240
cacaattatt gcagaaatcc agatggagac gtgagccctt ggtgctacgt ggccgagcat 300
gaggacggag tctactggaa gtactgtgaa attcctgcct gccagatgcc tggaaacctt 360
ggctgctaca aggatcatgg aaacccacct cctctcacgg gcaccagtaa aacctctaac 420
aagctcacca tacaaacctg tatcagcttc tgtcggagtc agagattcaa gtttgctggg 480
atggagtcag gctatgcctg cttctgtggg aacaatcctg actactggaa gcacggggag 540
gcggccagca ccgagtgcaa tagtgtctgc ttcggggacc acacgcagcc ctgcggtggg 600
gacggcagga ttatcctctt tgacactctc gtgggcgcct gcggtgggaa ctactcagcc 660
atggcagccg tggtgtactc ccctgacttc cctgacacct acgccactgg cagagtctgc 720
tactggacca tccgggttcc aggagcctct cgcatccatt tcaacttcac cctgtttgat 780
atcagggact ctgcagacat ggtggagctg ctggacggct acacccaccg cgtcctggtc 840
cggctcagtg ggaggagccg cccgcctctg tctttcaatg tctctctgga ttttgtcatt 900
ttgtatttct tctctgatcg catcaatcag gcccagggat ttgctgtgtt gtaccaagcc 960
accaaggagg aaccgccaca ggagagacct gctgtcaacc agaccctggc agaggtgatc 1020
accgagcaag ccaacctcag tgtcagcgct gcccactcct ccaaagtcct ctatgtcatc 1080
acccccagcc ccagccaccc tccgcagact gccccaggta gccattcctg ggcaccgtca 1140

-continued gttggggcca acagccacag agtggaagga tggactgtgt acggcctggc gaccctcctc 1200
atcctcacag tcacagcagt tgtcgcaaag attcttctgc atgtcacatt taaatctcat 1260
cgagtccctg catcaggaga ccttagggac tgtcgtcagc ctggggcttc tggagatatc 1320
tggaccattt tctatgaacc ttccactaca atctccatct ttaagaagaa gctcaagggt 1380
cagagtcaac aagatgaccg caatcccctc gtgagtgact ga 1422

<210> SEQ ID NO 2
<211> LENGTH: 1422
<212> TYPE: DNA
<213> ORGANISM: Homo sapiens

<400> SEQUENCE: 2
atggcgccgc cagccgcccg cctcgccctg ctctccgccg cggcgctcac gctggcggcc 60
cggcccgcgc ctagccccgg cctcggcccc gagtgtttca cagccaatgg tgcggattat 120
aggggaacac agaactggac agcactacaa ggcgggaagc catgtctgtt ttggaacgag 180
actttccagc atccatacaa cactctgaaa taccccaacg gggagggggg cctgggtgag 240
cacaactatt gcagaaatcc agatggagac gtgagcccct ggtgctatgt ggcagagcac 300
gaggatggtg tctactggaa gtactgtgag atacctgctt gccagatgcc tggaaacctt 360
ggctgctaca aggatcatgg aaacccacct cctctaactg gcaccagtaa aacgtccaac 420
aaactcacca tacaaacttg catcagtttt tgtcggagtc agaggttcaa gtttgctggg 480
atggagtcag gctatgcttg cttctgtgga aacaatcctg attactggaa gtacggggag 540
gcagccagta ccgaatgcaa cagcgtctgc ttcggggatc acacccaacc ctgtggtggc 600
gatggcagga tcatcctctt tgacactctc gtgggcgcct gcggtgggaa ctactcagcc 660
atgtcttctg tggtctattc ccctgacttc cccgacacct atgccacggg gagggtctgc 720
tactggacca tccgggttcc gggggcctcc cacatccact tcagcttccc cctatttgac 780
atcagggact cggcggacat ggtggagctt ctggatggct acacccaccg tgtcctagcc 840
cgcttccacg ggaggagccg cccacctctg tccttcaacg tctctctgga cttcgtcatc 900
ttgtatttct tctctgatcg catcaatcag gcccagggat ttgctgtttt ataccaagcc 960
gtcaaggaag aactgccaca ggagaggccc gctgtcaacc agacggtggc cgaggtgatc 1020
acggagcagg ccaacctcag tgtcagcgct gcccggtcct ccaaagtcct ctatgtcatc 1080
accaccagcc ccagccaccc acctcagact gtcccaggta gcaattcctg ggcgccaccc 1140
atgggggctg gaagccacag agttgaagga tggacagtct atggtctggc aactctcctc 1200
atcctcacag tcacagccat tgtagcaaag atacttctgc acgtcacatt caaatcccat 1260
cgtgttcctg cttcagggga ccttagggat tgtcatcaac cagggacttc gggggaaatc 1320
tggagcattt tttacaagcc ttccacttca atttccatct ttaagaagaa actcaagggt 1380
cagagtcaac aagatgaccg caatcccctt gtgagtgact aa 1422

<210> SEQ ID NO 3
<211> LENGTH: 1386
<212> TYPE: DNA
<213> ORGANISM: Mus musculus

<400> SEQUENCE: 3
atggggacac cacatctgca gggcttcctc ctcctcttcc cattgctgct gcggctgcac 60
ggggcctcag cagggagcct gcacagtcca ggcttgtccg aatgcttcca ggtgaacggc 120
gctgactacc gaggccacca gaactacacc ggcccacgcg gagctggacg cccttgtctt 180

-continued

```
ttctgggacc agacacagca gcacagctac agcagcgcca gcgaccctca gggccgctgg    240

gggttgggtg cgcataactt ctgtaggaac ccagacggtg atgtgcagcc ctggtgctac    300

gtggcagaga cagaagaggg catctactgg cgctactgtg atatccccac atgtcacatg    360

cctgggtacc tgggctgctt cgtggactct ggggcacccc ctgctctcag tggtcccagt    420

ggcacctcca caaagctcac tgtccaagtg tgccttcgat tctgccgcat gaagggctac    480

cagctggctg gtgtggaggc tggttatgcc tgcttctgtg gctctgaaag tgacctggcc    540

cgcggacgtc cagcccctgc caccgactgt gaccagatct gttttggcca cccaggccag    600

ctctgtggag gcgatggacg actaggcatc tatgaagtgt ctgtgggctc ctgccaggga    660

aactggtcgg ctcctcaagg agtcatctac tccccggatt ttccggatga gtatggacca    720

gaccggaact gcagctgggt attgggccaa ctgggcgctg tgctagaact caccttccgc    780

ctcttcgagt tggctgattc tcgagaccgg ctggagctac gcgacgtctc gtccggcaac    840

ctactccgtg ccttcgacgg cgcccatccg ccgcctccgg gaccgctgcg cctgcgcact    900

gctgcgctgc tgctcacctt ccgcagcgac gcaagaggcc atgctcaagg cttcgcgctc    960

acctaccgcg ggctgcagga tacagtggag ggcagagcat ctccagagga ttcaactgag   1020

agtctcgcag gggaccccga tggggctaac gcgagctgca gccccaagcc cggagctgca   1080

caggcttcga taggtgcccg agtcttctcc accgtgacgg ccttctctgt gctgctgctg   1140

ttgctcctgt ccctactgcg tttgctgcgt cgacggagct gtctgctggc tccaggaaaa   1200

gggtctctgg ccatgggacc ttcccggggc cccgggagaa gctgggctgt gtggtaccgc   1260

cggccccgag ggtggccct gccctgtccc ccaggggact ctcaggctga gggtcctgct   1320

gcgggctacc gtcccctgag tgcctccagc cagagctcct tgcgctcgct cgtctctgct   1380

ctctga                                                             1386
```

```
<210> SEQ ID NO 4
<211> LENGTH: 1428
<212> TYPE: DNA
<213> ORGANISM: Homo sapiens

<400> SEQUENCE: 4

atggggacac aagccctgca gggcttcctc tttctcctct tcctcccgct gctgcagccg     60

cgtggggcct cggctgggag cctgcacagt ccaggcctgt ccgaatgctt ccaggtgaat    120

ggggctgact accgcggcca ccagaaccgc actggcccgc gcggggcggg ccgcccgtgc    180

ctcttctggg accagacgca gcaacacagc tacagcagcg ccagcgaccc ccacggccgc    240

tgggggctgg gcgcgcacaa cttctgccgt aacccagacg gtgacgtgca gccgtggtgc    300

tacgtggctg agacagagga gggcatctac tggcgctact gcgacatccc ctcctgtcac    360

atgccaggct acctgggatg ctttgtggac tcaggggcac cccagccct cagcggcccc     420

agcggcacct ccacgaagct cacggtccag gtgtgcctac gcttctgccg catgaagggg    480

taccagctgg cgggcgtgga ggccggttac gcctgcttct gtggctctga aagcgacctg    540

gcccggggac gcctggcccc cgccaccgac tgtgaccaga tctgtttcgg ccaccctgga    600

cagctgtgtg gcggcgatgg gcggctgggc gtctatgaag tgtcggtggg ctcctgccag    660

gggaactgga cagcgcctca gggcgtcatc tactccccgg acttcccgga cgagtacggg    720

ccggaccgga actgcagctg ggccctgggc ccgccaggcg ccgcgctgga gctcaccttc    780

cgcctcttcg agctggccga cccgcgcgac cggctggagc tgcgcgacgc ggcttcgggc    840

agcctgctcc gcgccttcga tggcgcccgc ccaccgccgt ccgggccgct gcgcctgggc    900
```

-continued

```
actgccgcgc tgctgctcac cttccgaagc gacgcgcgcg gccacgcgca aggcttcgcg    960

ctcacctacc gcgggctgca ggacgccgct gaggacccag aggcccccga gggctcggcc   1020

cagacccccg cggcgcccct cgacggggcc aacgtgagct gcagccccag gcctggggct   1080

ccgccggccg cgattggggc ccgggtcttc tcgacggtga cggctgtctc ggtgctgctg   1140

ctgctgctcc tggggctgct gcgtccgctg cgccgacggt gcggggcgct ggggcagggc   1200

ctgagggcgg accggtggag ctgtctgctg gctccgggaa aagggccccc ggcgctgggg   1260

gcttccaggg gccccaggag aagctgggct gtgtggtacc aacagccccg aggggtggcc   1320

ttgccctgct cccccgggga cccccaggct gagggttctg ccgcgggcta ccggcctctg   1380

agtgcctcca gccagagctc cctgcgctcg ctcatctccg ctctctga                1428


<210> SEQ ID NO 5
<211> LENGTH: 473
<212> TYPE: PRT
<213> ORGANISM: Mus musculus

<400> SEQUENCE: 5

Met Ala Pro Pro Ala Ala Arg Leu Ala Leu Leu Ser Ala Ala Ala Leu
  1               5                  10                  15

Thr Leu Ala Ala Arg Pro Ala Pro Gly Pro Arg Ser Gly Pro Glu Cys
             20                  25                  30

Phe Thr Ala Asn Gly Ala Asp Tyr Arg Gly Thr Gln Ser Trp Thr Ala
         35                  40                  45

Leu Gln Gly Gly Lys Pro Cys Leu Phe Trp Asn Glu Thr Phe Gln His
     50                  55                  60

Pro Tyr Asn Thr Leu Lys Tyr Pro Asn Gly Glu Gly Gly Leu Gly Glu
 65                  70                  75                  80

His Asn Tyr Cys Arg Asn Pro Asp Gly Asp Val Ser Pro Trp Cys Tyr
                 85                  90                  95

Val Ala Glu His Glu Asp Gly Val Tyr Trp Lys Tyr Cys Glu Ile Pro
            100                 105                 110

Ala Cys Gln Met Pro Gly Asn Leu Gly Cys Tyr Lys Asp His Gly Asn
        115                 120                 125

Pro Pro Pro Leu Thr Gly Thr Ser Lys Thr Ser Asn Lys Leu Thr Ile
    130                 135                 140

Gln Thr Cys Ile Ser Phe Cys Arg Ser Gln Arg Phe Lys Phe Ala Gly
145                 150                 155                 160

Met Glu Ser Gly Tyr Ala Cys Phe Cys Gly Asn Asn Pro Asp Tyr Trp
                165                 170                 175

Lys His Gly Glu Ala Ala Ser Thr Glu Cys Asn Ser Val Cys Phe Gly
            180                 185                 190

Asp His Thr Gln Pro Cys Gly Gly Asp Gly Arg Ile Ile Leu Phe Asp
        195                 200                 205

Thr Leu Val Gly Ala Cys Gly Gly Asn Tyr Ser Ala Met Ala Ala Val
    210                 215                 220

Val Tyr Ser Pro Asp Phe Pro Asp Thr Tyr Ala Thr Gly Arg Val Cys
225                 230                 235                 240

Tyr Trp Thr Ile Arg Val Pro Gly Ala Ser Arg Ile His Phe Asn Phe
                245                 250                 255

Thr Leu Phe Asp Ile Arg Asp Ser Ala Asp Met Val Glu Leu Leu Asp
            260                 265                 270

Gly Tyr Thr His Arg Val Leu Val Arg Leu Ser Gly Arg Ser Arg Pro
        275                 280                 285
```

-continued

```
Pro Leu Ser Phe Asn Val Ser Leu Asp Phe Val Ile Leu Tyr Phe Phe
    290                 295                 300

Ser Asp Arg Ile Asn Gln Ala Gln Gly Phe Ala Val Leu Tyr Gln Ala
305                 310                 315                 320

Thr Lys Glu Glu Pro Pro Gln Glu Arg Pro Ala Val Asn Gln Thr Leu
                325                 330                 335

Ala Glu Val Ile Thr Glu Gln Ala Asn Leu Ser Val Ser Ala Ala His
            340                 345                 350

Ser Ser Lys Val Leu Tyr Val Ile Thr Pro Ser Pro Ser His Pro Pro
        355                 360                 365

Gln Thr Ala Pro Gly Ser His Ser Trp Ala Pro Ser Val Gly Ala Asn
    370                 375                 380

Ser His Arg Val Glu Gly Trp Thr Val Tyr Gly Leu Ala Thr Leu Leu
385                 390                 395                 400

Ile Leu Thr Val Thr Ala Val Val Ala Lys Ile Leu Leu His Val Thr
                405                 410                 415

Phe Lys Ser His Arg Val Pro Ala Ser Gly Asp Leu Arg Asp Cys Arg
            420                 425                 430

Gln Pro Gly Ala Ser Gly Asp Ile Trp Thr Ile Phe Tyr Glu Pro Ser
        435                 440                 445

Thr Thr Ile Ser Ile Phe Lys Lys Lys Leu Lys Gly Gln Ser Gln Gln
    450                 455                 460

Asp Asp Arg Asn Pro Leu Val Ser Asp
465                 470


<210> SEQ ID NO 6
<211> LENGTH: 473
<212> TYPE: PRT
<213> ORGANISM: Homo sapiens

<400> SEQUENCE: 6

Met Ala Pro Pro Ala Ala Arg Leu Ala Leu Leu Ser Ala Ala Ala Leu
  1               5                  10                  15

Thr Leu Ala Ala Arg Pro Ala Pro Ser Pro Gly Leu Gly Pro Glu Cys
             20                  25                  30

Phe Thr Ala Asn Gly Ala Asp Tyr Arg Gly Thr Gln Asn Trp Thr Ala
         35                  40                  45

Leu Gln Gly Gly Lys Pro Cys Leu Phe Trp Asn Glu Thr Phe Gln His
     50                  55                  60

Pro Tyr Asn Thr Leu Lys Tyr Pro Asn Gly Glu Gly Gly Leu Gly Glu
 65                  70                  75                  80

His Asn Tyr Cys Arg Asn Pro Asp Gly Asp Val Ser Pro Trp Cys Tyr
                 85                  90                  95

Val Ala Glu His Glu Asp Gly Val Tyr Trp Lys Tyr Cys Glu Ile Pro
            100                 105                 110

Ala Cys Gln Met Pro Gly Asn Leu Gly Cys Tyr Lys Asp His Gly Asn
        115                 120                 125

Pro Pro Pro Leu Thr Gly Thr Ser Lys Thr Ser Asn Lys Leu Thr Ile
    130                 135                 140

Gln Thr Cys Ile Ser Phe Cys Arg Ser Gln Arg Phe Lys Phe Ala Gly
145                 150                 155                 160

Met Glu Ser Gly Tyr Ala Cys Phe Cys Gly Asn Asn Pro Asp Tyr Trp
                165                 170                 175

Lys Tyr Gly Glu Ala Ala Ser Thr Glu Cys Asn Ser Val Cys Phe Gly
            180                 185                 190
```

```
Asp His Thr Gln Pro Cys Gly Gly Asp Gly Arg Ile Ile Leu Phe Asp
        195                 200                 205

Thr Leu Val Gly Ala Cys Gly Gly Asn Tyr Ser Ala Met Ser Ser Val
    210                 215                 220

Val Tyr Ser Pro Asp Phe Pro Asp Thr Tyr Ala Thr Gly Arg Val Cys
225                 230                 235                 240

Tyr Trp Thr Ile Arg Val Pro Gly Ala Ser His Ile His Phe Ser Phe
                245                 250                 255

Pro Leu Phe Asp Ile Arg Asp Ser Ala Asp Met Val Glu Leu Leu Asp
            260                 265                 270

Gly Tyr Thr His Arg Val Leu Ala Arg Phe His Gly Arg Ser Arg Pro
        275                 280                 285

Pro Leu Ser Phe Asn Val Ser Leu Asp Phe Val Ile Leu Tyr Phe Phe
    290                 295                 300

Ser Asp Arg Ile Asn Gln Ala Gln Gly Phe Ala Val Leu Tyr Gln Ala
305                 310                 315                 320

Val Lys Glu Glu Leu Pro Gln Glu Arg Pro Ala Val Asn Gln Thr Val
                325                 330                 335

Ala Glu Val Ile Thr Glu Gln Ala Asn Leu Ser Val Ser Ala Ala Arg
            340                 345                 350

Ser Ser Lys Val Leu Tyr Val Ile Thr Thr Ser Pro Ser His Pro Pro
        355                 360                 365

Gln Thr Val Pro Gly Ser Asn Ser Trp Ala Pro Pro Met Gly Ala Gly
    370                 375                 380

Ser His Arg Val Glu Gly Trp Thr Val Tyr Gly Leu Ala Thr Leu Leu
385                 390                 395                 400

Ile Leu Thr Val Thr Ala Ile Val Ala Lys Ile Leu Leu His Val Thr
                405                 410                 415

Phe Lys Ser His Arg Val Pro Ala Ser Gly Asp Leu Arg Asp Cys His
            420                 425                 430

Gln Pro Gly Thr Ser Gly Glu Ile Trp Ser Ile Phe Tyr Lys Pro Ser
        435                 440                 445

Thr Ser Ile Ser Ile Phe Lys Lys Lys Leu Lys Gly Gln Ser Gln Gln
    450                 455                 460

Asp Asp Arg Asn Pro Leu Val Ser Asp
465                 470


<210> SEQ ID NO 7
<211> LENGTH: 461
<212> TYPE: PRT
<213> ORGANISM: Mus musculus

<400> SEQUENCE: 7

Met Gly Thr Pro His Leu Gln Gly Phe Leu Leu Leu Phe Pro Leu Leu
  1               5                  10                  15

Leu Arg Leu His Gly Ala Ser Ala Gly Ser Leu His Ser Pro Gly Leu
             20                  25                  30

Ser Glu Cys Phe Gln Val Asn Gly Ala Asp Tyr Arg Gly His Gln Asn
         35                  40                  45

Tyr Thr Gly Pro Arg Gly Ala Gly Arg Pro Cys Leu Phe Trp Asp Gln
     50                  55                  60

Thr Gln Gln His Ser Tyr Ser Ser Ala Ser Asp Pro Gln Gly Arg Trp
 65                  70                  75                  80

Gly Leu Gly Ala His Asn Phe Cys Arg Asn Pro Asp Gly Asp Val Gln
                 85                  90                  95
```

```
Pro Trp Cys Tyr Val Ala Glu Thr Glu Glu Gly Ile Tyr Trp Arg Tyr
            100                 105                 110

Cys Asp Ile Pro Thr Cys His Met Pro Gly Tyr Leu Gly Cys Phe Val
        115                 120                 125

Asp Ser Gly Ala Pro Pro Ala Leu Ser Gly Pro Ser Gly Thr Ser Thr
    130                 135                 140

Lys Leu Thr Val Gln Val Cys Leu Arg Phe Cys Arg Met Lys Gly Tyr
145                 150                 155                 160

Gln Leu Ala Gly Val Glu Ala Gly Tyr Ala Cys Phe Cys Gly Ser Glu
                165                 170                 175

Ser Asp Leu Ala Arg Gly Arg Pro Ala Pro Ala Thr Asp Cys Asp Gln
            180                 185                 190

Ile Cys Phe Gly His Pro Gly Gln Leu Cys Gly Gly Asp Gly Arg Leu
        195                 200                 205

Gly Ile Tyr Glu Val Ser Val Gly Ser Cys Gln Gly Asn Trp Ser Ala
    210                 215                 220

Pro Gln Gly Val Ile Tyr Ser Pro Asp Phe Pro Asp Glu Tyr Gly Pro
225                 230                 235                 240

Asp Arg Asn Cys Ser Trp Val Leu Gly Gln Leu Gly Ala Val Leu Glu
                245                 250                 255

Leu Thr Phe Arg Leu Phe Glu Leu Ala Asp Ser Arg Asp Arg Leu Glu
            260                 265                 270

Leu Arg Asp Val Ser Ser Gly Asn Leu Leu Arg Ala Phe Asp Gly Ala
        275                 280                 285

His Pro Pro Pro Pro Gly Pro Leu Arg Leu Arg Thr Ala Ala Leu Leu
    290                 295                 300

Leu Thr Phe Arg Ser Asp Ala Arg Gly His Ala Gln Gly Phe Ala Leu
305                 310                 315                 320

Thr Tyr Arg Gly Leu Gln Asp Thr Val Glu Gly Arg Ala Ser Pro Glu
                325                 330                 335

Asp Ser Thr Glu Ser Leu Ala Gly Asp Pro Asp Gly Ala Asn Ala Ser
            340                 345                 350

Cys Ser Pro Lys Pro Gly Ala Ala Gln Ala Ser Ile Gly Ala Arg Val
        355                 360                 365

Phe Ser Thr Val Thr Ala Phe Ser Val Leu Leu Leu Leu Leu Leu Ser
    370                 375                 380

Leu Leu Arg Leu Leu Arg Arg Arg Ser Cys Leu Leu Ala Pro Gly Lys
385                 390                 395                 400

Gly Ser Leu Ala Met Gly Pro Ser Arg Gly Pro Gly Arg Ser Trp Ala
                405                 410                 415

Val Trp Tyr Arg Arg Pro Arg Gly Val Ala Leu Pro Cys Pro Pro Gly
            420                 425                 430

Asp Ser Gln Ala Glu Gly Pro Ala Ala Gly Tyr Arg Pro Leu Ser Ala
        435                 440                 445

Ser Ser Gln Ser Ser Leu Arg Ser Leu Val Ser Ala Leu
    450                 455                 460


<210> SEQ ID NO 8
<211> LENGTH: 475
<212> TYPE: PRT
<213> ORGANISM: Homo sapiens

<400> SEQUENCE: 8

Met Gly Thr Gln Ala Leu Gln Gly Phe Leu Phe Leu Leu Phe Leu Pro
  1               5                  10                  15
```

-continued

```
Leu Leu Gln Pro Arg Gly Ala Ser Ala Gly Ser Leu His Ser Pro Gly
            20                  25                  30

Leu Ser Glu Cys Phe Gln Val Asn Gly Ala Asp Tyr Arg Gly His Gln
        35                  40                  45

Asn Arg Thr Gly Pro Arg Gly Ala Gly Arg Pro Cys Leu Phe Trp Asp
    50                  55                  60

Gln Thr Gln Gln His Ser Tyr Ser Ser Ala Ser Asp Pro His Gly Arg
 65                  70                  75                  80

Trp Gly Leu Gly Ala His Asn Phe Cys Arg Asn Pro Asp Gly Asp Val
                85                  90                  95

Gln Pro Trp Cys Tyr Val Ala Glu Thr Glu Glu Gly Ile Tyr Trp Arg
            100                 105                 110

Tyr Cys Asp Ile Pro Ser Cys His Met Pro Gly Tyr Leu Gly Cys Phe
        115                 120                 125

Val Asp Ser Gly Ala Pro Pro Ala Leu Ser Gly Pro Ser Gly Thr Ser
    130                 135                 140

Thr Lys Leu Thr Val Gln Val Cys Leu Arg Phe Cys Arg Met Lys Gly
145                 150                 155                 160

Tyr Gln Leu Ala Gly Val Glu Ala Gly Tyr Ala Cys Phe Cys Gly Ser
                165                 170                 175

Glu Ser Asp Leu Ala Arg Gly Arg Leu Ala Pro Ala Thr Asp Cys Asp
            180                 185                 190

Gln Ile Cys Phe Gly His Pro Gly Gln Leu Cys Gly Gly Asp Gly Arg
        195                 200                 205

Leu Gly Val Tyr Glu Val Ser Val Gly Ser Cys Gln Gly Asn Trp Thr
    210                 215                 220

Ala Pro Gln Gly Val Ile Tyr Ser Pro Asp Phe Pro Asp Glu Tyr Gly
225                 230                 235                 240

Pro Asp Arg Asn Cys Ser Trp Ala Leu Gly Pro Pro Gly Ala Ala Leu
                245                 250                 255

Glu Leu Thr Phe Arg Leu Phe Glu Leu Ala Asp Pro Arg Asp Arg Leu
            260                 265                 270

Glu Leu Arg Asp Ala Ala Ser Gly Ser Leu Leu Arg Ala Phe Asp Gly
        275                 280                 285

Ala Arg Pro Pro Pro Ser Gly Pro Leu Arg Leu Gly Thr Ala Ala Leu
    290                 295                 300

Leu Leu Thr Phe Arg Ser Asp Ala Arg Gly His Ala Gln Gly Phe Ala
305                 310                 315                 320

Leu Thr Tyr Arg Gly Leu Gln Asp Ala Ala Glu Asp Pro Glu Ala Pro
                325                 330                 335

Glu Gly Ser Ala Gln Thr Pro Ala Ala Pro Leu Asp Gly Ala Asn Val
            340                 345                 350

Ser Cys Ser Pro Arg Pro Gly Ala Pro Pro Ala Ala Ile Gly Ala Arg
        355                 360                 365

Val Phe Ser Thr Val Thr Ala Val Ser Val Leu Leu Leu Leu Leu Leu
    370                 375                 380

Gly Leu Leu Arg Pro Leu Arg Arg Arg Cys Gly Ala Leu Gly Gln Gly
385                 390                 395                 400

Leu Arg Ala Asp Arg Trp Ser Cys Leu Leu Ala Pro Gly Lys Gly Pro
                405                 410                 415

Pro Ala Leu Gly Ala Ser Arg Gly Pro Arg Arg Ser Trp Ala Val Trp
            420                 425                 430

Tyr Gln Gln Pro Arg Gly Val Ala Leu Pro Cys Ser Pro Gly Asp Pro
        435                 440                 445
```

-continued

```
Gln Ala Glu Gly Ser Ala Ala Gly Tyr Arg Pro Leu Ser Ala Ser Ser
    450                 455                 460

Gln Ser Ser Leu Arg Ser Leu Ile Ser Ala Leu
465                 470                 475


<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

gtgcttcaca gccaacggtg ca                                              22


<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

acgtagcacc aagggctcac gt                                              22


<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

agggaaactg gtcggctc                                                   18


<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

aaggcacgga gtaggttgc                                                  19
```